(12) United States Patent
Rovin et al.

(10) Patent No.: US 8,313,950 B2
(45) Date of Patent: Nov. 20, 2012

(54) HEPCIDINS AS BIOMARKERS FOR IMPENDING LUPUS NEPHRITIS FLARE

(75) Inventors: Brad H. Rovin, Columbus, OH (US); Xiaolan Zhang, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 353 days.

(21) Appl. No.: 12/600,890

(22) PCT Filed: May 19, 2008

(86) PCT No.: PCT/US2008/006407
§ 371 (c)(1), (2), (4) Date: Nov. 19, 2009

(87) PCT Pub. No.: WO2008/144041
PCT Pub. Date: Nov. 27, 2008

(65) Prior Publication Data
US 2010/0151487 A1    Jun. 17, 2010

Related U.S. Application Data

(60) Provisional application No. 60/931,053, filed on May 21, 2007.

(51) Int. Cl.
*G01N 33/493*  (2006.01)
*A61K 38/10*  (2006.01)
*A61K 38/17*  (2006.01)

(52) U.S. Cl. ............... 436/86; 530/324; 530/326

(58) Field of Classification Search ............... None
See application file for complete search history.

(56) References Cited

U.S. PATENT DOCUMENTS

| | | | |
|---|---|---|---|
| 7,320,894 B2 | 1/2008 | Kulaksiz et al. | |
| 2004/0096990 A1 | 5/2004 | Geacintov et al. | |
| 2005/0148025 A1 | 7/2005 | Lehmann et al. | |
| 2005/0148029 A1 | 7/2005 | Buechler et al. | |
| 2006/0019339 A1* | 1/2006 | Lauth et al. | 435/69.1 |
| 2009/0173876 A1* | 7/2009 | Li et al. | 250/282 |

OTHER PUBLICATIONS

Malyszko, J. et al. "Hepcidin, Iron Status, and Renal Function in Chronic Renal Failure, Kidney Transplantation, and Hemodialysis" American Journal of Hematology 81:832-837 (2006).*
Rovin et al. "Biomarkers for Lupus Nephritis: The Quest Continues" Clin J Am Soc Nephrol 4: 1858-1865, 2009.*
Zhang et al. "Biomarkers of lupus nephritis determined by serial urine proteomics" Kidney International (2008) 74, 799-807.*
Zhang et al. "A composite urine biomarker reflects interstitial inflammation in lupus nephritis kidney biopsies" Kidney International (2012) 81, 401-406.*
Avihingsanon, et al., Measurement of Urinary Chemokine and Growth Factor Messenger RNA's: A Noninvasive Monitoring in Lupus Nephritis, Kidney International, 2006, vol. 69, pp. 747-753.
Malyszko, J. et al., Hepcidin in Anemia and Inflammation in Chronic Kidney Disease, Kidney & Blood Pressure Research, 2007, 30: pp. 15-30.
Oates, J. et al., Prediction of urinary protein markers in lupus nephritis, Kidney International, Dec. 2005, 68(6): pp. 2588-2592.
Rovin, B. et al., Urine Chemokines as Biomarkers of Human Systemic Lupus Erythematosus Activity, American Society of Nephrology, 2005, 16: pp. 467-473.
Rovin, B. et al., Plasma, urine, and renal expression of adiponectin in human systemic lupus erythematosus, Kidney International, vol. 68 (2005), pp. 1825-1833.
PCT/US08/06407, May 19, 2008, Notification of Transmittal of the International Search Report and Written Opinion, Date of mailing Jul. 22, 2008.
PCT/US2008/006407, May 19, 2008, Notification Concerning Transmittal of International Preliminary Report on Patentability, Date of mailing Dec. 3, 2009.

* cited by examiner

*Primary Examiner* — Christine Foster
(74) *Attorney, Agent, or Firm* — MacMillan, Sobanski & Todd, LLC

(57) ABSTRACT

Biomarkers for determining a kidney flare episode in systemic lupus erythematosus are described.

7 Claims, 10 Drawing Sheets
(4 of 10 Drawing Sheet(s) Filed in Color)

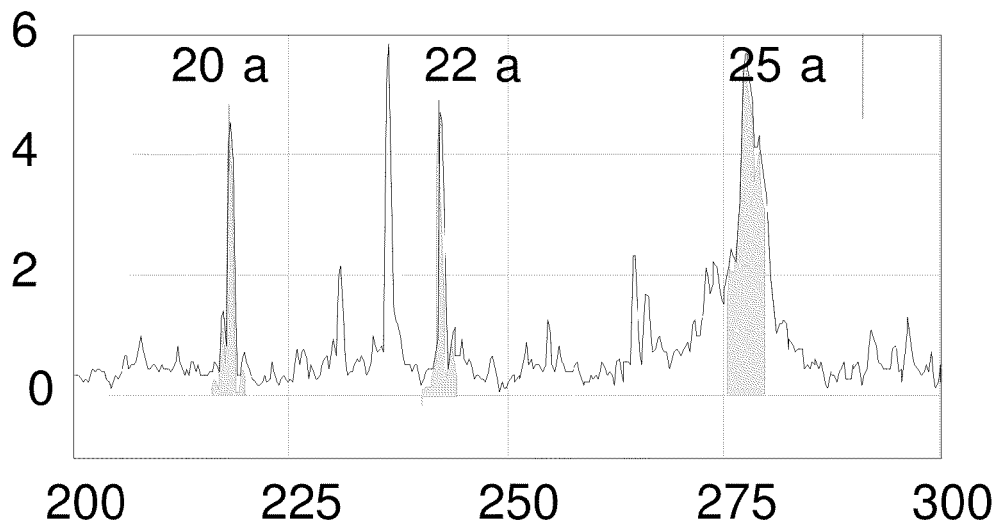
Figure 4A
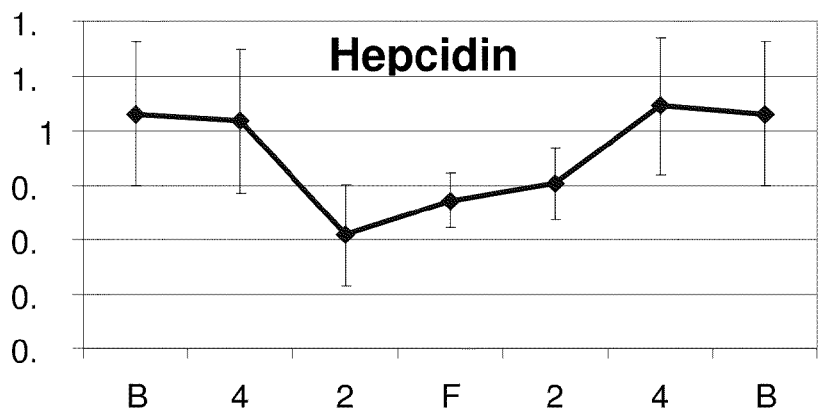
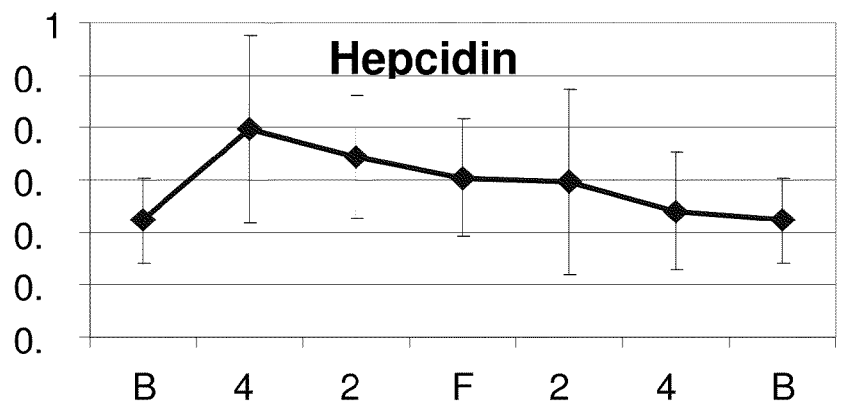
Figure 4B

Table 1 - SELDI Protein Ions showing Differential Expression between SLE Renal Flare States

| No | Peak | M/Z[2] | ID | Frequency[3] | 4-/B[3] | 2-/B | 2+/B | 4+/B | F/4- | F/2- | F/2+ | F/4+ | 2+/4+ |
|---|---|---|---|---|---|---|---|---|---|---|---|---|---|
| 1 | M1 | 2010 | | 0.32 | | | | | | | | 2.7 | 2.1 |
| 2 | M4 | 2094 | | 0.48 | 1.6 | | | | | | | | |
| 3 | M8 | 2198 | Hepcidin | 0.72 | 1.5 | | | | | | | | |
| 4 | M11 | 2274 | | 0.36 | | 3.6 | 2.8 | | | | | | |
| 5 | M15 | 2364 | | 0.48 | 3.1 | | | 1.4 | | | | | |
| 6 | M16 | 2380 | | 0.76 | 1.2 | | | | | | 1.6 | | |
| 7 | M17 | 2395 | A1AT | 0.84 | 2.1 | | | | | 2.1 | | 2.3 | |
| 8 | M18 | 2411 | | 0.52 | | | | | | | | 2.4 | |
| 9 | M21 | 2500 | | 0.64 | | | | | | 1.8 | | | |
| 10 | M26 | 2648 | Albumin | 0.76 | 1.94 | | | | | | | | |
| 11 | M28 | 2686 | | 0.84 | | | 1.7 | | | | | | |
| 12 | M34 | 2797 | Hepcidin | 0.6 | | | | | 0.6 | | | | |
| 13 | M58 | 3398 | | 0.72 | 2.0 | | | | | | | | |
| 14 | M70 | 3712 | | 0.92 | 1.7 | | | | | | | | |
| 15 | M74 | 3827 | | 0.44 | 1.9 | | | | | | | | |
| 16 | M77 | 3886 | | 0.32 | 1.9 | | | | | | | | |
| 17 | M85 | 4058 | | 0.6 | 1.7 | | | | | | | | |
| 18 | M87 | 4096 | | 0.4 | | | | | | | | | 0.7 |
| 19 | M89 | 4132 | | 0.72 | 1.7 | | | | | | | | |
| 20 | M93 | 4248 | | 0.32 | 2.3 | | | | | | | 1.6 | 0.6 |
| 21 | M95 | 4293 | | 0.56 | 1.1 | | | | | | | | |
| 22 | M101 | 4427 | | 0.56 | 1.5 | | | | | | | | |
| 23 | M105 | 4540 | | 0.4 | | | | | | 0.4 | | | |
| 24 | M123 | 5080 | | 0.36 | | | | | 0.5 | | | | |
| 25 | M125 | 5225 | | 0.36 | | | | | | | | | |
| 26 | M137 | 5700 | | 0.36 | | | | | | | | | 1.6 |
| 27 | M161 | 8018 | | 0.72 | | | | 1.4 | | | | | |

1. All protein ions are statistically significant with p < 0.05, and the highlighted numbers denote p<0.01. 2. B stands for Baseline. F for Flare. 4- for 4 months pre-flare. 2- for 2 months pre-flare. 2+ for 2 months post-flare, and 4+ for 4 months post-flare. 3. Frequency indicates the percent of patients having the peak in the urine. 4. Fold change between groups is done in the indicated time order, e.g. 4-/B stands for relative peak intensity at 4 months preflare divided by the intensity at baseline.

Figure 8

| Table 2 - Frequency of Combined Protein Ions in SLE Flare States |||||||||||
|---|---|---|---|---|---|---|---|---|---|---|
| Comparison Groups | Individual Protein Ion with Frequency |||||||||  Combined Frequency |
|  | M15 | M16 | M17 | M28 | M34 | M58 | M70 | M95 | M161 |  |
|  | 48% | 76% | 84% | 84% | 60% | 72% | 92% | 56% | 72% |  |
|  |  |  |  | √ |  | √ |  |  |  | 100% |
|  | √ |  |  |  |  |  | √ |  |  | 100% |
| Remission and Pre-Flare |  |  | √ |  |  |  | √ |  |  | 100% |
|  |  |  |  |  |  | √ | √ |  |  | 100% |
|  |  |  |  |  |  |  | √ | √ |  | 100% |
|  |  | √ | √ |  |  |  |  |  |  | 100% |
| Flare and Post Flare |  |  | √ | √ |  |  |  |  |  | 100% |
|  |  |  | √ |  |  |  |  |  | √ | 100% |

Figure 9

HEPCIDINS AS BIOMARKERS FOR IMPENDING LUPUS NEPHRITIS FLARE

GOVERNMENT SUPPORT

The invention was made with government support from the National Institutes of Health research grants NIH-NIDDK Grant Number DK55546. The government may have certain rights in the invention.

RELATED APPLICATIONS

This application is a 371 filing of PCT/US08/06407, filed May 19, 2008, which claims priority to U.S. Provisional Patent Application 60/931,053, filed May 21, 2007, the disclosure of which is expressly incorporated herein by reference, in its entirety.

SEQUENCE LISTING

The instant application contains a Sequence Listing which has been submitted in ASCII format via EFS-Web and is hereby incorporated by reference in its entirety. Said ASCII copy, created on May 24, 2012, is named 604_29096_SEQ_LIST_OSU-2007-106.txt and is 1,189 bytes in size.

BACKGROUND

Systemic lupus erythematosus (SLE) is characterized by periods of illness, called flares, and periods of wellness, or remission. While the warning signs of a flare in a patient can include one or more of increased fatigue, pain, rash, fever, abdominal discomfort, headache and dizziness, by the time the patient is experiencing these symptoms, there is already further damage being inflicted on the patient's body, and in particular, the kidney.

Systemic lupus erythematosus tends to be chronic and relapsing, often with symptom-free periods that can last for years. Since the course and episodes (i.e., flare-ups) of acute systemic lupus erythematosus is unpredictable, the prognosis varies widely. It has been found, however, that if the initial inflammation is controlled, the long-term prognosis is good. Therefore, early detection and treatment of kidney damage caused by systemic lupus erythematosus can reduce the incidence of severe kidney disease.

Therefore, there is a need for the early treatment of flares to help such patients with lupus maintain better health.

If there is an early detection of a flare, certain therapies, such as, for example, the drug therapy of cyclophosphamide combined with prednisone, can be initiated to help delay or prevent kidney failure, a serious complication of lupus.

Presently there are no clinically useful biomarkers that can be readily used to predict an impending flare-up of such serious lupus kidney disorders is systemic lupus erythematosus.

The expectation is that the earlier any kidney involvement is detected and treated, and the faster remission is induced, the better the prognosis for kidney function. Also, earlier detection and treatment, before the systemic lupus erythematosus disease becomes full-blown, is anticipated to decrease the duration and intensity of any treatment that would be needed. This would decrease the morbidity and mortality of the highly toxic immunosuppressive therapies that are standardly used to treat systemic lupus erythematosus nephritis.

What are lacking are tools for predicting the likelihood that a particular patient will suffer from a flare-up of systemic lupus erythematosus nephritis. In particular, there are no known identifying predictors to determine when a patient will suffer from such flare-up.

Also lacking are tools for profiling factors influencing sensitivity and resistance of patients to systemic lupus erythematosus therapeutic agents. Such tools would be predictive of treatment response of a patient to a particular drug, and would allow for increased predictability regarding chemosensitivity or chemoresistance of such patients to enable the design of optimal treatment regimens for individual patients. Such tools would likewise enable the identification of new drugs.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

SUMMARY

In one aspect, there is provided herein a system for predicting an impending flare of lupus kidney disease. The system includes a non-invasive and easily accessible method for monitoring kidney activity to forecast a flare-up of systemic lupus erythematosus in a patient suffering from such disease.

A method of providing efficacy information for selected drugs for treatment of a patient comprises:
(a) comparing a level of hepcidin from a patient urine with a database including records comprising baseline levels of hepcidin from the same patient herein; and
(b) providing a suitable drug when the levels of hepcidin are different from the baseline levels of hepcidin.

A machine-readable medium includes program instructions for performing the following steps:
(a) comparing a level of hepcidin from a patient urine with a database including records comprising baseline levels of hepcidin from the same patient herein; and
(b) providing a suitable drug when the levels of hepcidin are different from the baseline levels of hepcidin.

A method of selecting a therapy for a patient comprises:
(a) providing a subject baseline hepcidin profile of a sample from the patient;
(b) providing a plurality of reference profiles, each associated with a point in time; and
(c) selecting at least one therapy when a predetermined difference between the baseline hepcidin level and the heuristic measured levels is at, or within a predetermined range, to thereby select a therapy for the patient.

The method can further comprise administering the therapy selected in step (c) above to the patient. The method can also include where the most similar reference profile is selected by weighting a comparison value for each value of the plurality using a weight value.

An array comprises a substrate having a plurality of addresses where each address has disposed thereon a capture probe that can specifically bind to one or more of the hepcidin compositions described herein. The capture probe can bind to one or more of the hepcidin under stringent conditions. Each hepcidin bound by the capture probe of each address is unique among the plurality of addresses.

A computer-readable medium comprises a plurality of digitally-encoded expression profiles where each profile of the plurality has a plurality of values, and each value represents the expression of a different hepcidin as described herein.

A kit for evaluating a drug comprises:

an array having a substrate including a plurality of addresses where each address has disposed thereon a capture probe that can specifically bind at least one hepcidin described herein;

a computer-readable medium having a plurality of digitally-encoded expression profiles where each profile of the plurality has a plurality of values and each value represents the expression of at least one hepcidin detected by the array.

A method for diagnosing, aiding in diagnosis of sensitivity or resistance a therapeutic agent for systemic lupus erythematosus, and for evaluating the efficacy of a therapeutic agent for systemic lupus erythematosus in a subject comprises comparing the expression of one or more biomarkers in a sample from a subject to a predetermined standard for each the one or more biomarkers; wherein the one or more biomarkers are selected from the group including hepcidin-25 and hepcidin-20; and wherein a significant difference in the expression of the one or more biomarkers in the sample as compared to a predetermined standard of each the one or more biomarkers diagnoses or aids in the diagnosis of a flare-up of a systemic lupus erythematosus kidney activity disorder.

The method can include where the predetermined standard corresponds to: (a) the expression levels of the biomarker in healthy subjects, or (b) the expression levels of the biomarker in non systemic lupus erythematosus sensitive samples from different subjects in a same phenotypic group.

The method can comprise comparing the expression of two or more biomarkers, wherein the diagnosis is based on a score-based classification method. For example, the method can comprise comparing the expression of different biomarkers; wherein each biomarker is assigned a score of 0 or 1, wherein a biomarker is assigned a score of 0 if the expression of the biomarker is not significantly different from the expression of the biomarker in a predetermined standard and wherein a biomarker is assigned a score of 1 if the expression of the biomarker is significantly different from the expression of the biomarker in a predetermined standard; wherein the subject is assigned an overall score which corresponds to the sum of the assigned scores from different markers; and wherein a given threshold (t) is used to diagnose or aid in the diagnosis.

The method can comprise comparing the expression of two or more biomarkers, where the diagnosis is made by comparing the expression profile of the two or more biomarkers to a predetermined standard profile for the biomarkers, and wherein a difference in the profiles diagnoses or aids in the diagnosis.

The predetermined standard profile can be determined by comparing the expression of the two or more biomarkers in subjects to the expression of the two or more biomarkers in healthy subjects using a machine learning technique.

The predetermined standard profile can be determined by comparing the expression of the two or more biomarkers in subjects and in healthy subjects using support vector machines, K-nearest neighbor classifier, or classification tree analysis.

The method can comprise comparing the expression of one or more biomarkers in a sample from a subject to the expression of the one or more biomarkers in a sample obtained from the subject at a subsequent point in time; wherein the one or more biomarkers are selected from the group consisting of hepcidin-20 and hepcidin-25, where a difference in the expression of the one or more biomarker diagnoses or aids in the diagnosis of the progression of one or more such diseases in the subject. The method can include comparing the expression of two or more biomarkers.

A method to screen for a candidate compound useful to treat a systemic lupus erythematosus implicated disease comprising: (a) identifying a candidate compound which regulates the expression of one or more biomarkers that include hepcidin-20 and hepcidin-25; and (b) determining whether such candidate compound is effective to treat systemic lupus erythematosus.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention can be more fully understood from the following detailed description, the drawings and the Sequence Descriptions that form a part of this application. The sequence descriptions and Sequence Listing attached hereto comply with the rules governing nucleotide and/or amino acid sequence disclosures in patent applications as set forth in 37 CFR §§1.821-1.825. The Sequence Descriptions contain the three letter codes for amino acids as defined in 37 CFR §§1.821-1.825, which are incorporated herein by reference.

FIG. 2A—The spectra of a whole flare cycle are presented between the 2000 and 10 000 Dalton region. The LMW urine proteome shows an overall increase in peaks between 2000 and 4000 Dalton as flare approaches, which then decrease during flare treatment. Peak intensity (relative protein abundance) is given on the y-axis.

FIG. 2B—The spectra from 4 months pre-flare and flare of a Class IV GN patient showing that some protein ions decrease at the flare.

FIGS. 4A-4E depict urine hepcidin expression in SLE Nephritis:

FIG. 4A—Typical urine SELDI spectrum in a class IV LN urine showing three hepcidin isoforms of 20, 22 and 25 at m/z of 2197, 2432 and 2798, respectively.

FIG. 4B—Time course of hepcidin 20 and 25 expression (mean relative intensities) during the SLE nephritis flare cycle. Error bars indicate standard errors.

FIG. 4C—On-chip CID fragmentation of peak 34, used to identify the ion as hepcidin 25.

FIG. 4D—MS fragments of trypsin-digested hepcidin 25 standard. FIG. 4D discloses SEQ ID NO: 3.

FIG. 4E—LC/MS/MS detection of the internal peptide of hepcidin 25 (y-ions are labeled) in the urine of an SLE nephritis patient. FIG. 4E discloses SEQ ID NO: 3.

FIG. 5A—SELDI relative intensity of M17 (A1AT) and M26 (Albumin) between baseline and flare, and baseline and 4 month pre-flare.

FIG. 5B—SELDI spectrum of M17 at flare.

FIG. 5C—SELDI spectrum of M26 pre-flare.

Figure 6A:
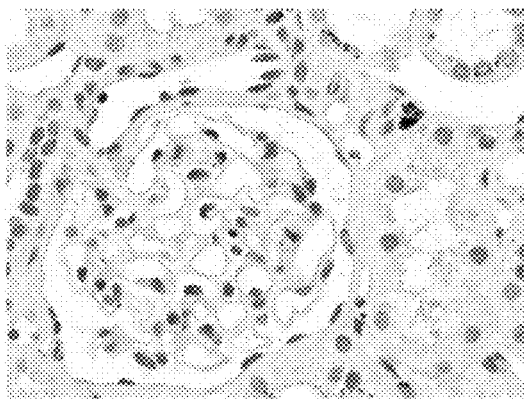
FIGS. 6A-6D depict intrarenal expression of hepcidin. Immunohistochemical staining for hepcidin is shown for renal biopsy material from a normal kidney (FIG.
Figure 6B:
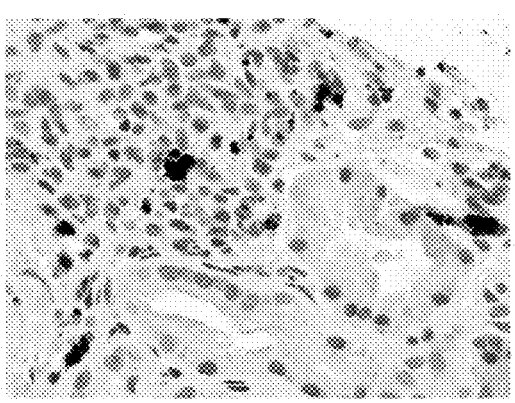
Figure 6C:
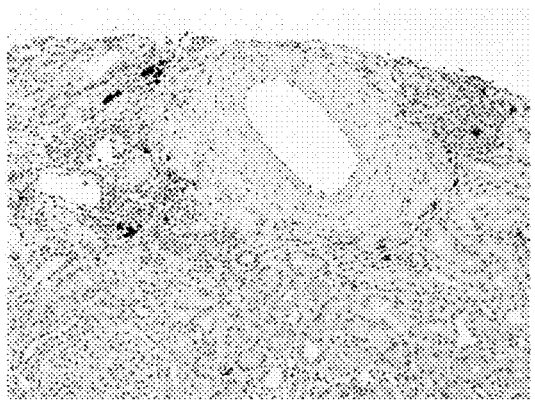
Figure 6D:
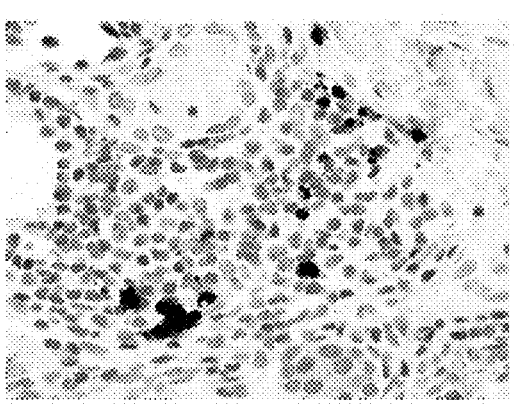

6A—Cont), and three patients with class IV SLE nephritis (FIGS. 6B-6D—SLE). The positive cells are infiltrating interstitial leukocytes.

Figure 7A:
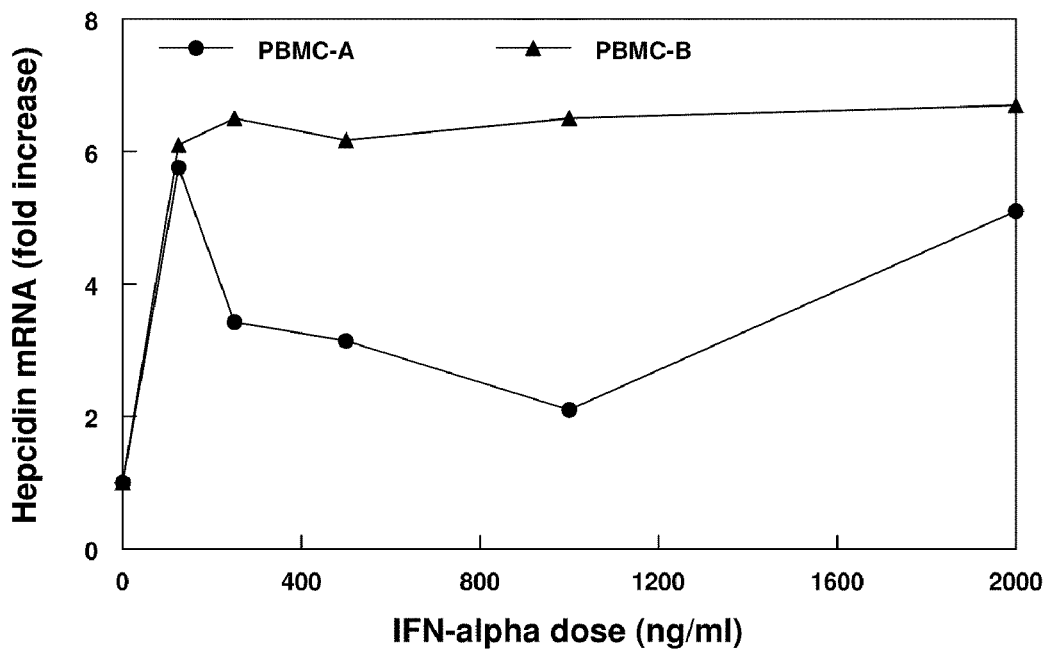
Figure 7B:
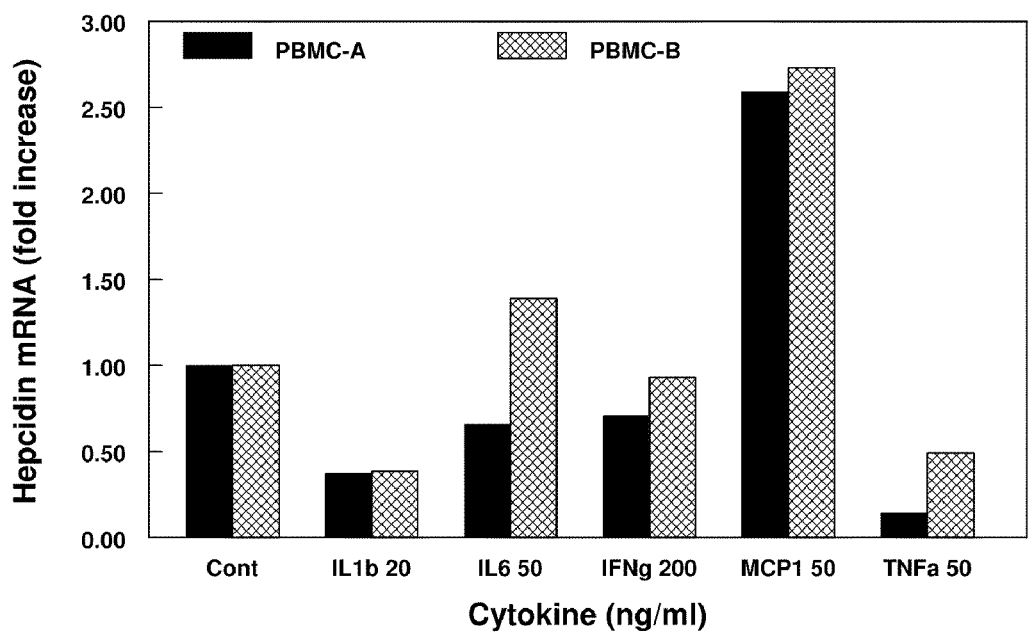

FIGS. 7A and 7B depict cytokine modulation of hepcidin expression in PBMC:

FIG. 7A—Hepcidin mRNA (fold increase) as a function of INF-alpha dose (ng/ml).

FIG. 7B—Hepcidin mRNA (fold change) in response to various inflammatory cytokines.

FIG. 8 depicts Table 1—SELDI protein ions showing differential expression between SLE renal flare states.

FIG. 9—Table 2—Frequency of combined protein ions in SLE flare states.

DETAILED DESCRIPTION OF THE INVENTION

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

All publications, patent applications, patents, and other references mentioned herein are incorporated by reference in their entirety. The disclosure of all patents, patent applications (and any patents that issue thereon, as well as any corresponding published foreign patent applications), GenBank and other accession numbers and associated data, and publications mentioned throughout this description are hereby incorporated by reference herein. It is expressly not admitted, however, that any of the documents incorporated by reference herein teach or disclose the present invention.

The present invention may be understood more readily by reference to the following detailed description of the embodiments of the invention and the Examples included herein. However, before the present methods, compounds and compositions are disclosed and described, it is to be understood that this invention is not limited to specific methods, specific cell types, specific host cells or specific conditions, etc., as such may, of course, vary, and the numerous modifications and variations therein will be apparent to those skilled in the art. It is also to be understood that the terminology used herein is for the purpose of describing specific embodiments only and is not intended to be limiting.

DEFINITIONS

Unless otherwise defined, all technical and scientific terms used herein have the same meaning as commonly understood by one of ordinary skill in the art to that this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

The disclosure of all patents, patent applications (and any patents that issue thereon, as well as any corresponding published foreign patent applications), GenBank and other accession numbers and associated data, and publications mentioned throughout this description are hereby incorporated by reference herein. It is expressly not admitted, however, that any of the documents incorporated by reference herein teach or disclose the present invention.

The present invention may be understood more readily by reference to the following detailed description of the embodiments of the invention and the Examples included herein. However, before the present methods, compounds and compositions are disclosed and described, it is to be understood that this invention is not limited to specific methods, specific cell types, specific host cells or specific conditions, etc., as such may, of course, vary, and the numerous modifications and variations therein will be apparent to those skilled in the art. It is also to be understood that the terminology used herein is for the purpose of describing specific embodiments only and is not intended to be limiting.

It is to be noted herein that the specification lists the accession numbers for the known genes, whereby the full sequences of the genes may be referenced, and which are expressly incorporated herein by reference thereto as of the filing of this application for patent.

As used herein and in the appended claims, the singular forms "a," "and," and "the" include plural referents unless the context clearly dictates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

"Nucleic acid," when used herein, refers to deoxyribonucleotides or ribonucleotides, nucleotides, oligonucleotides, polynucleotide polymers and fragments thereof in either single- or double-stranded form. A nucleic acid may be of natural or synthetic origin, double-stranded or single-stranded, and separate from or combined with carbohydrate, lipids, protein, other nucleic acids, or other materials, and may perform a particular activity such as transformation or form a useful composition such as a peptide nucleic acid (PNA). Unless specifically limited, the term encompasses nucleic acids containing known analogues of natural nucleotides that have similar binding properties as the reference nucleic acid and may be metabolized in a manner similar to naturally-occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19: 5081; Ohtsuka et al. (1985) J. Biol. Chem. 260: 2605-2608; Cassol et al. (1992); Rossolini et al. (1994) Mol. Cell. Probes 8: 91-98). The term nucleic acid is used interchangeably with gene, cDNA, and mRNA encoded by a gene.

An "Oligonucleotide" or "oligo" is a nucleic acid and is substantially equivalent to the terms amplimer, primer, oligomer, element, target, and probe, and may be either double or single stranded.

"Plurality" refers to a group of at least two or more members.

"Polynucleotide" refers to nucleic acid having a length from 25 to 3,500 nucleotides.

"Probe" or "Polynucleotide Probe" refers to a nucleic acid capable of hybridizing under stringent conditions with a target region of a target sequence to form a polynucleotide probe/target complex. Probes comprise polynucleotides that are 15 consecutive nucleotides in length. Probes may be 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 6, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 polynucleotides in length. In some embodiments, probes are 70 nucleotides in length. Probes may be less than 100% complimentary to a target region, and may comprise sequence alterations in the form of one or more deletions, insertions, or substitutions, as compared to probes that are 100% complementary to a target region.

"Purified," when used herein in the context of nucleic acids or proteins, denotes that a nucleic acid or protein gives rise to essentially one band in an electrophoretic gel. Particularly, it means that the nucleic acid or protein is at least 50, 55, 60, 65, 70, 75, 80, 85, 90, 91, 92, 93, 94, 95, 96, 97, 98, 99 or 100% pure with respect to the presence of any other nucleic acid or protein species.

"Test sample" refers to a sample of bodily fluid obtained for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. A sample may comprise a bodily fluid; a cell; an extract from a cell, chromosome, organelle, or membrane isolated from a cell; genomic DNA, RNA, or cDNA in solution or bound to a substrate; or a biological tissue or biopsy thereof. A sample may be obtained from any bodily fluid (blood, serum, plasma, urine, cerebrospinal fluid saliva, phlegm, gastric juices, sputum, pleural effusions, etc.), cultured cells, biopsies, or other tissue preparations. In addition, one of skill in the art would realize that some test samples would be more readily analyzed following a fractionation or purification procedure, for example, separation of whole blood into serum or plasma components.

"Plurality" refers to at least two. In certain embodiments, a plurality refers to at least 3, more preferably at least 5, even more preferably at least 10, even more preferably at least 15, and most preferably at least 20. In particularly preferred embodiments, a plurality is a large number, i.e., at least 100.

"Subject" refers to a human or non-human organism. Thus, the methods and compositions described herein are applicable to both human and veterinary disease. Further, while a subject is preferably a living organism, the invention described herein may be used in post-mortem analysis as well. Preferred subjects are "patients," i.e., living humans that are receiving medical care. This includes persons with no defined illness who are being investigated for signs of pathology.

"Diagnosis" refers to methods by which the skilled artisan can estimate and/or determine whether or not a patient is suffering from a given disease or condition. The skilled artisan often makes a diagnosis on the basis of one or more diagnostic indicators, i.e., a marker, the presence, absence, or amount of which is indicative of the presence, severity, or absence of the condition. Also, a prognosis is often determined by examining one or more "prognostic indicators." These are markers, the presence or amount of which in a patient (or a sample obtained from the patient) signal a probability that a given course or outcome will occur. For example, when one or more prognostic indicators reach a sufficiently high level in samples obtained from such patients, the level may signal that the patient is at an increased probability for experiencing a future flare-up of systemic lupus erythematosus in comparison to a similar patient exhibiting a lower marker level. A level or a change in level of a prognostic indicator, which in turn is associated with an increased probability of morbidity or death, is referred to as being "associated with an increased predisposition to an adverse outcome" in a patient. Preferred prognostic markers can predict the onset of a flare-up in a patient, or the chance of future flare-up.

"Correlating," is used in reference to the use of diagnostic and markers, refers to comparing the presence or amount of the marker(s) in a patient to its presence or amount in persons known to suffer from, or known to be at risk of, a given condition; or in persons known to be free of a given condition. A marker level in a patient sample can be compared to a level known to be associated with a specific diagnosis. The sample's marker level is said to have been correlated with a diagnosis; that is, the skilled artisan can use the marker level to determine whether the patient suffers from a specific type diagnosis, and respond accordingly. Alternatively, the sample's marker level can be compared to a marker level known to be associated with a good outcome (e.g., the absence of disease, etc.). In certain embodiments, a profile of marker levels are correlated to a global probability or a particular outcome using ROC curves.

"Determining the diagnosis" refers to methods by which the skilled artisan can determine the presence or absence of a particular disease in a patient. The term "diagnosis" does not refer to the ability to determine the presence or absence of a particular disease with 100% accuracy, or even that a given course or outcome is more likely to occur than not. Instead, the skilled artisan will understand that the term "diagnosis" refers to an increased probability that a certain disease is present in the subject. In certain embodiments, a diagnosis indicates about a 5% increased chance that a disease is present, about a 10% chance, about a 15% chance, about a 20% chance, about a 25% chance, about a 30% chance, about a 40% chance, about a 50% chance, about a 60% chance, about a 75% chance, about a 90% chance, and about a 95% chance. The term "about" in this context refers to +/−2%.

"Stringent hybridization conditions" and "stringent hybridization wash conditions" in the context of nucleic acid hybridization experiments such as Southern and Northern hybridizations are sequence dependent, and are different under different environmental parameters.

Nucleic acids having longer sequences hybridize specifically at higher temperatures. An extensive guide to the hybridization of nucleic acids is found in Tijssen (1993) Laboratory Techniques in Biochemistry and Molecular Biology—Hybridization with Nucleic Acid Probes part I chapter 2 "Overview of principles of hybridization and the strategy of nucleic acid probe assays," Elsevier, N.Y. Generally, highly stringent hybridization and wash conditions are selected to be 5° C. lower than the thermal melting point ($T_m$) for the specific sequence at a defined ionic strength and pH. Typically, under "stringent conditions" a probe will hybridize to its target subsequence, but to no other sequences. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids that have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., 10 to 50 nucleotides), stringent conditions typically involve salt concentrations of less than 1.0 M Na ion, typically 0.01 to 1.0 M Na ion concentration (or other salts) at pH 7.0 to 8.3, and the temperature is typically at least 30° C. Stringent conditions can also be achieved with the addition of destabilizing agents such as formamide. In general, a signal to noise ratio of 2.times. (or higher) than that observed for an unrelated probe in the particular hybridization assay indicates detection of a specific hybridization. Nucleic acids that do not hybridize to each other under stringent conditions are still substantially similar if the polypeptides that they encode are substantially similar. This occurs, e.g., when a copy of a nucleic acid is created using the maximum codon degeneracy permitted by the genetic code.

"Substrate" refers to a support, such as a rigid or semi-rigid support, to which nucleic acid molecules or proteins are applied or bound, and includes membranes, filters, chips, slides, wafers, fibers, magnetic or nonmagnetic beads, gels, capillaries or other tubing, plates, polymers, and microparticles, and other types of supports, which may have a variety of surface forms including wells, trenches, pins, channels and pores.

Array Construction

The nucleic acid sequences can be used in the construction of arrays, for example, microarrays. Methods for construction of microarrays, and the use of such microarrays, are known in the art, examples of which can be found in U.S. Pat. Nos. 5,445,934, 5,744,305, 5,700,637, and 5,945,334, the entire disclosure of each of which is hereby incorporated by reference. Microarrays can be arrays of nucleic acid probes, arrays of peptide or oligopeptide probes, or arrays of chimeric probes—peptide nucleic acid (PNA) probes. Those of skill in the art will recognize the uses of the collected information.

One particular example, the in situ synthesized oligonucleotide Affymetrix GeneChip system, is widely used in many research applications with rigorous quality control standards. (Rouse R. and Hardiman G., "Microarray technology—an intellectual property retrospective," Pharmacogenomics 5:623-632 (2003).). Currently the Affymetrix GeneChip uses eleven 25-oligomer probe pair sets containing both a perfect match and a single nucleotide mismatch for each gene sequence to be identified on the array. Using a light-directed chemical synthesis process (photolithography technology), highly dense glass oligo probe array sets (>1,000,000 25-oligomer probes) can be constructed in a about 3×3-cm plastic cartridge that serves as the hybridization chamber. The ribonucleic acid to be hybridized is isolated, amplified, fragmented, labeled with a fluorescent reporter group, and stained with fluorescent dye after incubation. Light is emitted from the fluorescent reporter group only when it is bound to the probe. The intensity of the light emitted from the perfect match oligoprobe, as compared to the single base pair mismatched oligoprobe, is detected in a scanner, which in turn is analyzed by bioinformatics software (www.affymetrix.com). The GeneChip system provides a standard platform for array fabrication and data analysis, which permits data comparisons among different experiments and laboratories.

Microarrays according to the invention can be used for a variety of purposes, as further described herein, including but not limited to, screening for the resistance or susceptibility of a patient to a drug based on the genetic expression profile of the patient.

Also, it is to be understood that methods using Western blot and/or RT-PCR are especially useful and are also known in the art.

From the discussion and the Examples herein, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein, will be apparent to those skilled in the art from the foregoing description. Such modifications are also intended to fall within the scope of the appended claims. All publications, including patents and non-patent literature, referred to in this specification are expressly incorporated by reference herein.

EXAMPLES

Accordingly, the disclosure provides methods of identifying flare-up episode of kidney nephritis in a patient suffering from Systemic Lupus Erythematosus (SLE).

Methods for identifying a flare-up of systemic lupus erythematosus kidney activity in a patient are described herein. In a particular aspect, the method includes identifying heuristic changes in a hepatic peptide hormone, hepcidin which is a key regulator of iron metabolism. Hepcidin is a peptide that is made primarily in the liver, distributed in plasma and excreted in urine. Hepcidin may also be detected in ascites fluid and cyst fluid, tissues and organs such as liver, and in specific cells, such as macrophages. It may also be made in the kidney.

Hepcidin is the homeostatic regulator of intestinal iron absorption, iron recycling by macrophages, and iron mobilization from hepatic stores. Hepcidin acts by inhibiting the efflux of iron through ferroportin, the iron exporter of enterocytes, macrophages and hepatocytes. As an iron-regulatory hormone, the synthesis of hepcidin is increased by iron loading and decreased by anemia and hypoxia.

Hepcidin was identified as a 25 amino acid peptide (hepcidin-25) in human plasma and urine, exhibiting antimicrobial activity. The full-length hepcidin precursor is an 84 amino acid protein (SwissProt Accession No. P81172) comprising a signal sequence and a pro-region (see Kulaksiz, H. et al. (2004) Gut 53:735-743). The hepcidin-25 and hepcidin-20 markers are derived from the C-terminus of the full-length hepcidin protein. Hepcidin is recognized by antibodies available from, e.g., U.S. Biological (catalog H2008-51) (www.usbio.net, Swampscott, Mass.). In one aspect, two variants of hepcidin are especially useful as biomarkers, hepcidin-25 and hepcidin-20.

The amino acid sequences of hepcidin-25 and hepcidin-20 are:

```
                                             [SEQ ID NO: 1]
Hepcidin-25 - DTHFPICIFCCGCCHRSKCGMCCKT,
and

[SEQ ID NO: 2]
Hepcidin-20 - ICIFCCGCCHRSKCGMCCKT.
```

The hepcidin markers are further characterized by their binding properties on chromatographic surfaces. Hepcidin binds to cation exchange adsorbents (e.g., the Ciphergen® CM10 ProteinChip® array).

In another aspect, there is provided a method which comprises collecting a plurality of samples from a subject over time, and thereafter determining any change in levels of expression of one or more of hepcidin-20 and hepcidin-25, which are markers for systemic lupus erythematosus kidney activity.

The method further comprises comparing the hepcidin expression profiles of a baseline level with one or more subsequent levels to determine whether there is an altered expression of any of the hepcidin levels.

In one aspect, there is provided a method of analyzing a subject sample for one or more subject-derived markers selected to identify at least a beginning of a kidney flare episode in a patient suffering from systemic lupus erythematosus, comprising: assaying the sample for the presence or amount of one or more subject-derived markers related to a kidney flare episode, and characterizing the subject's risk of having or the kidney flare episode disorders based upon the presence or amount of the marker, wherein the amount of at least one of the one or more subject-derived markers is not compared to a predetermined threshold amount. The characterization step can be performed without comparing the amount of any of the marker(s) related to inflammation to a predetermined threshold amount.

In a particular aspect, the subject-derived marker(s) are selected from the group consisting of hepcidin-25 and hepcidin-20. The subject sample can be selected from the group consisting of a blood sample, a serum sample, a plasma sample, and a urine sample.

It is understood that proteins frequently exist in a sample in a plurality of different forms. When detecting or measuring a protein in a sample, the ability to differentiate between different forms of a protein depends upon the nature of the difference and the detection method that is used. In particular, a sandwich immunoassay, having two antibodies directed against different epitopes on a protein, is useful to detect all forms of the protein that contain both epitopes and will not detect those forms that contain only one of the epitopes. As disclosed herein, one or more forms of the hepcidin protein are better marker than certain other forms. In a particular embodiment, it is useful to employ an assay method that distinguishes between forms of a protein and that specifically detects and measures a desired form or forms of the protein.

Mass spectrometry is an especially useful method to distinguish between different forms of the hepcidin protein since the different forms typically have different masses that can be resolved by mass spectrometry. It has been discovered that one or more forms of the hepcidin protein are especially good markers for detecting an impending kidney nephritis flare-up episode in systemic lupus erythematosus and that mass spectrometry is able to specifically detect and measure the useful forms. Various forms of mass spectrometry are useful for detecting the protein forms, including laser desorption approaches, such as SELDI.

Thus, in certain embodiments, when reference is made herein to detecting a particular protein or to measuring the amount of a particular protein, it means detecting and measuring the protein and resolving various forms of protein. The measuring of hepcidin-25 and hepcidin-20 is the measuring and differentiating between various forms of the hepcidin protein. In particular, when it is desired to measure a particular form or forms of a protein, e.g., a particular form of hepcidin, the particular form (or forms) is specified. For example, "measuring hepcidin-25" means measuring hepcidin-25 in a way that distinguishes it from other forms of hepcidin, e.g., hepcidin-20.

In one embodiment, a sample is analyzed by means of a biochip. A biochip generally comprises a solid substrate having a substantially planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), and others.

One useful mass spectrometric technique for use in the invention is "Surface Enhanced Laser Desorption and Ionization" or "SELDI," as described, for example, in U.S. Pat. No. 5,719,060 and No. 6,225,047, both to Hutchens and Yip, which describes a method of desorption/ionization gas phase ion spectrometry (e.g., mass spectrometry) in which an analyte (here, one or more of the biomarkers) is captured on the surface of a SELDI mass spectrometry probe.

While the individual hepcidin-25 and hepcidin-20 markers are useful diagnostic biomarkers, it has been found that a combination of these two biomarkers can provide greater predictive value of a particular status than single biomarkers alone. Specifically, the detection of both markers in a sample can increase the sensitivity and/or specificity of the test. A combination of at least two markers is sometimes referred to as a "biomarker profile" or "biomarker fingerprint." Accordingly, hepcidin-25 and hepcidin-20 can be combined with other markers for improve the sensitivity and/or specificity of the diagnostic test.

In another aspect, there is provided herein methods for determining the impending remission of systemic lupus erythematosus and/or an impending kidney nephritis flare-up episode in a subject. Disease course refers to changes in disease status over time, including disease progression (worsening) and disease regression (improvement). Over time, the amounts or relative amounts (e.g., the pattern) of the biomarkers changes. Therefore, the trend of these markers, either increased or decreased over time toward diseased or non-diseased indicates the course of the disease. The method includes the measurement of one or more hepcidin markers in a subject for at least two different time points, e.g., a first time and a second time, and comparing the change in amounts, if any. The course of disease is determined based on these comparisons.

In another aspect, there is provided a method of analyzing a subject sample for one or more subject-derived markers selected to identify subjects suffering from a kidney nephritis flare-up episode, comprising: assaying the sample for the presence or amount of one or more subject-derived marker(s)

related to systemic lupus erythematosus selected from the group consisting of hepcidin-25, hepcidin-22 and hepcidin-20, and characterizing the subject's risk of suffering a kidney nephritis flare episode based upon the presence or amount of the markers, wherein the amount of each of the markers is not compared to a predetermined threshold amount.

In a particular aspect, the method for assigning a therapy regimen and/or assigning a prognosis to a subject diagnosed with or suspected of suffering from systemic lupus erythematosus, comprising: performing an assay method on a sample obtained from the subject, wherein the assay method provides one or more detectable signals related to the presence or amount of one or more subject-derived markers independently selected from the group consisting of markers related to kidney flare episodes, or markers related to the subject-derived markers; and correlating the signal(s) obtained from the assay method to ruling in or out a therapy regimen for the subject and/or assigning a prognosis to the subject.

In another particular aspect, there is provided a method which can be useful as a tool to rule in or out an assignment of the subject to an early goal-directed therapy.

In one particular method, the one or more subject-derived markers comprise at least one marker selected from the group consisting of hepcidin-25, hepcidin-22 and hepcidin-20, or one or more markers related to the subject-derived markers.

In another particular aspect, there is provided a method where the plurality of markers comprises at least one marker related to inflammation, and at least one marker related to nephritis or one or more markers related thereto.

In certain embodiments, the sample is from a human. Also, in certain embodiments, the sample is selected from the group consisting of blood, serum, urine, cerebrospinal fluid, and plasma.

In one embodiment, the method is useful to rule in or out one or more treatments for inclusion in a therapy regimen comprising administration of immunosuppressive therapy. In particular, a diagnostic method, comprising determining a concentration of hepcidin in a bodily fluid sample from a subject suffering from systemic lupus erythematosus, where an increase in hepcidin concentration in the bodily fluid sample relative to a threshold hepcidin concentration indicates a kidney flare episode in the subject, and where lack of an increase in hepcidin concentration in the bodily fluid sample relative to a threshold hepcidin concentration indicates a kidney flare episode is not present in the subject.

In a particular embodiment, the method further comprises determining a concentration of hepcidin-20 in a bodily fluid sample from the subject. An increase in hepcidin-20 concentration in the bodily fluid sample relative to a threshold hepcidin-20 concentration indicates a kidney flare episode in the subject, and a lack of an increase in hepcidin-20 concentration in the bodily fluid sample relative to a threshold hepcidin-20 concentration indicates a kidney flare episode is not present in the subject. In certain embodiments, the increase in hepcidin-20 is present at about four months prior to the presentation of symptoms of the kidney flare episode.

Also, in a particular embodiment, the method further comprises determining a concentration of hepcidin-25 in a bodily fluid sample from the subject. A decrease in hepcidn-25 concentration in the bodily fluid sample relative to a threshold hepcidin-25 concentration indicates a kidney flare episode in the subject, and a lack of an increase in hepcidin-25 concentration in the bodily fluid sample relative to a threshold hepcidin-25 concentration indicates a kidney flare episode is not present in the subject. In certain embodiments, the decrease in hepcidin-25 is present at about two months prior to the presentation of symptoms of the kidney flare episode.

In another aspect, there is provided a method for diagnosing a kidney flare-up disease condition characterized by non-physiological levels of hepcidin. The method includes obtaining a tissue or fluid sample from a subject; contacting the sample with an antibody or fragment thereof that specifically binds to one or more mid-portion or carboxy terminal epitopes of hepcidin, and quantifying hepcidin level in the sample; where the non-physiological level of hepcidin is indicative of the disease condition. In a particular aspect, the antibody specifically binds a mid-portion epitope contained within at least amino acids 20 to 25 of hepcidin.

In another aspect, there is provided a test device that includes a test surface comprising a plurality of discrete addressable locations corresponding to the hepcidin subject-derived markers, where each the location comprising an antibody immobilized at the location selected to bind for detection one of the subject-derived markers.

In another aspect, there is provided a kit for qualifying impending flare-ups of systemic lupus erythematosus status. The kits are useful to detect the hepcidin-25 and/or hepcidin-20 markers. The kit can include a solid support, such as a chip, a microtiter plate or a bead or resin having a capture reagent attached thereon, where the capture reagent binds the hepcidin-25 or hepcidin-20 marker. The kit can comprise mass spectrometry probes for SELDI, such as ProteinChip® arrays. The kit can also include a solid support with a reactive surface, and a container comprising the biospecific capture reagent. The kit can also include a washing solution or instructions for making a washing solution, such that the combination of the capture reagent and the washing solution allows capture of the biomarker or biomarkers on the solid support for subsequent detection by, e.g., mass spectrometry. The kit may include more than type of adsorbent, each present on a different solid support. The kit can also include instructions that may inform a consumer about how to collect the sample, how to wash the probe or the particular markers to be detected. In yet another embodiment, the kit can include one or more containers with the marker samples, to be used as standard(s) for calibration.

Thus, in a particular embodiment, the kit is especially useful for detecting an impending kidney nephritis flare-up episode characterized by non-physiological levels of hepcidin-25 and/or hepcidin-20. The kit includes anti-hepcidin-25 and/or anti-hepcidin-20 antibodies or fragments thereof that specifically bind to one or more mid-portion or carboxy terminal epitopes of hepcidin-25 and/or hepcidin-20, and a reagent that binds directly or indirectly to the antibody or fragment thereof.

One particular method for qualifying an impending kidney nephritis flare-up episode in a subject comprising:
 (a) measuring one or more biomarkers in a biological sample from the subject, wherein at least one biomarker is hepcidin; and
 (b) correlating the measurement or measurements with an impending kidney nephritis flare-up episode. In certain embodiments, the flare-up episode indicates class III or IV systemic lupus erythematosus nephritis.

The method can include measuring a plurality of biomarkers in the biological sample, where the plurality of biomarkers comprises hepcidin-20 and hepcidin-25.

In certain embodiments, the one or more biomarkers can be measured by mass spectrometry, such as SELDI-TOF. Also, the correlating can be performed by executing a software classification algorithm.

In another particular aspect, there is provided a method for reporting the status to the subject, and/or recording the status on a tangible medium.

In another particular aspect, there is provided a method for managing subject treatment based on such classification. Also, the method can further comprise measuring the at least one biomarker after subject management and correlating the measurement with systemic lupus erythematosus disease progression.

In a particular embodiment, the method includes (a) measuring, at a first time, one or more biomarkers in a biological sample from the subject, where at least one biomarker is hepcidin; (b) measuring, at a second time, at least one biomarker in a biological sample from the subject; and (c) comparing the first measurement and the second measurement; wherein the comparative measurements determine the course of the systemic lupus erythematosus.

Also provided herein is a kit for testing for systemic lupus erythematosus flare-up episodes that includes: (a) a solid support comprising at least one capture reagent attached thereto, wherein the capture reagent binds hepcidin; and (b) instructions for using the solid support to detect hepcidin. The solid support can comprise a capture reagent that is a SELDI probe and can also include a standard reference of hepcidin.

In another aspect, a software product can comprise a code that accesses data attributed to a sample, the data comprising measurement of at least one biomarker in the sample, wherein at least one biomarker is hepcidin; and code that executes a classification algorithm that classifies the systemic lupus erythematosus status of the sample as a function of the measurement. A method can include communicating to a subject a diagnosis relating to systemic lupus erythematosus status determined from the correlation of at least one biomarker in a sample from the subject, wherein at least one biomarker is hepcidin.

Methods of Predicting Response to Therapeutic Agents

In another aspect, there is provided herein a method of predicting the response of a patient suffering from systemic lupus erythematosus to treatment with a therapeutic agent. The method comprises contacting a sample obtained from the patient to measure the levels of expression of one or more of hepcidin-20 and hepcidin-25. The expression levels are then used to provide an expression profile for the patient that is then compared to the drug-gene correlations, wherein a positive correlation between a drug and expressed levels of hepcidin-20 and/or hepcidin-25 in the patient indicates that the patient would be sensitive to the drug, and wherein a negative correlation between a drug and the expressed levels of hepcidin-20 and/or hepcidin-25 in the patient indicates that the patient would not be responsive to the drug.

In some embodiments, the effectiveness of the agent's ability to alter chemosensitivity can be tested using standard assays. The agent is tested by conducting assays in that sample are co treated with the newly identified agent along with a previously known therapeutic agent. The choice of previously known therapeutic agent is determined based upon the gene-drug correlation between the gene or genes whose expression is affected by the new agent.

EXAMPLES

The invention may be better understood by reference to the following examples, which serve to illustrate but not to limit the present invention.

Results:

The LMW urine proteome from 25 moderate-severe SLE nephritis flare cycles in 19 patients was studied. These patients were all female, 53% were Caucasian, 42% African American, and 5% Asian. The patients' initial kidney biopsies showed class III (n=5), class IV (n=11), and class V (n=3) nephritis, and 27% of the flares were adjudicated as severe, while 73% were considered moderate.

Figure 2A:
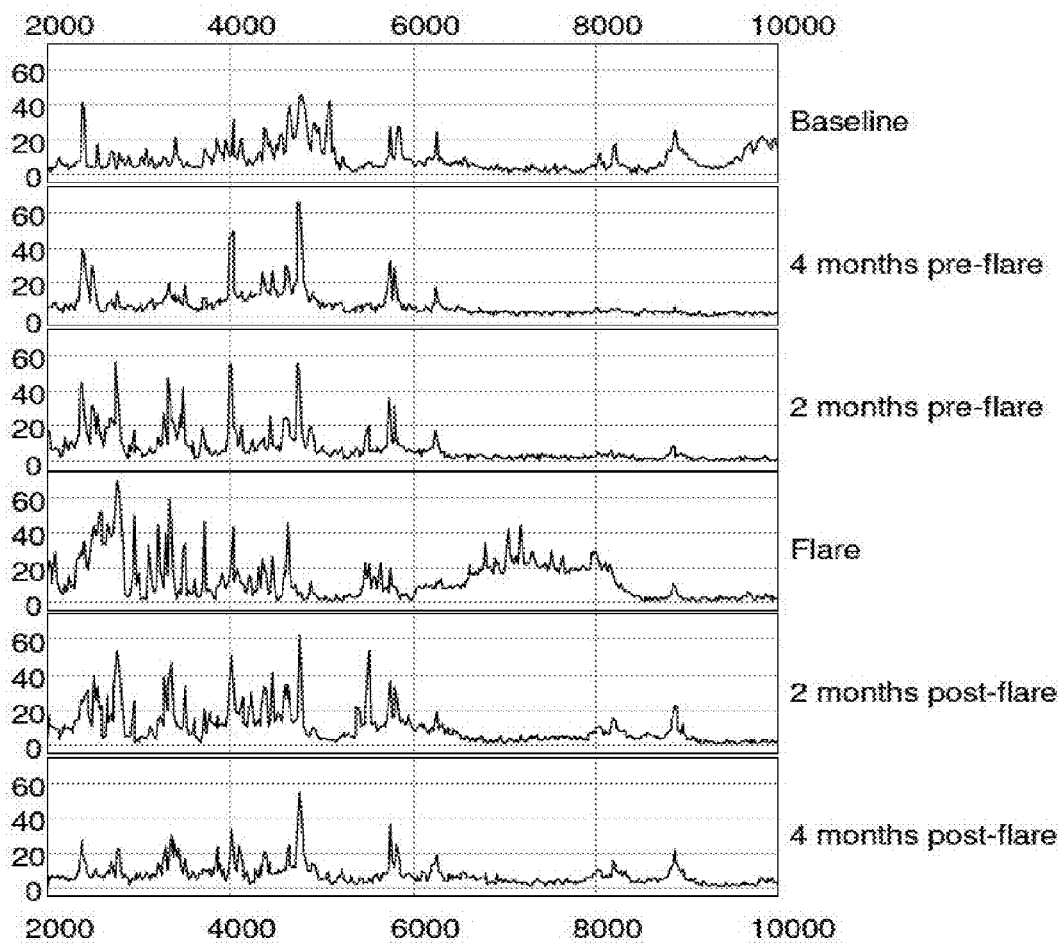
FIGS. 2A and 2B depict urine SELDI spectra of class IV SLE nephritis flare cycles.

SELDI-TOF-MS identified 176 protein peaks (m/z protein ions) between 2000 and 20 000 m/z, using a weak cation exchanger protein chip. Ninety-six protein ions were present in over 30% of the flare cycles, and 43 peaks were present in over 60% of the flare cycles. A typical SELDI-TOF-MS spectrum from a whole flare cycle is shown in FIG. 2A, illustrating how SELDI-TOF-MS spectra can capture dynamic changes in urine protein expression during the evolution of a lupus nephritis flare.

Figure 2B:
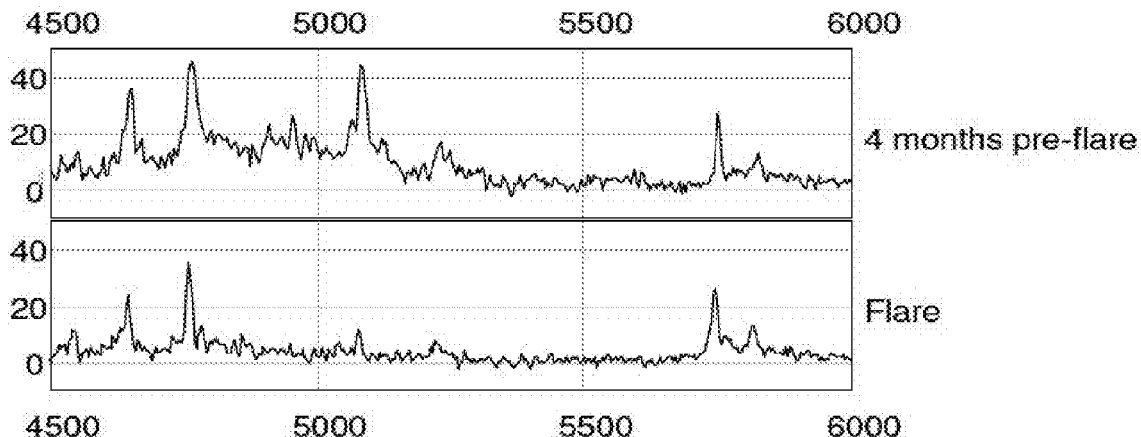
Figure 3A:
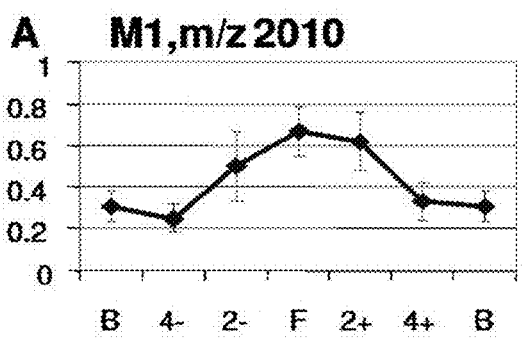
FIG. 3 depicts the expression of candidate urine biomarkers over time. The mean relative intensities of 4 differentially expressed protein ions (log-transformed data for M87) are plotted at several points of the renal flare cycle. Error bars indicate standard errors (A-D).
Figure 3B:
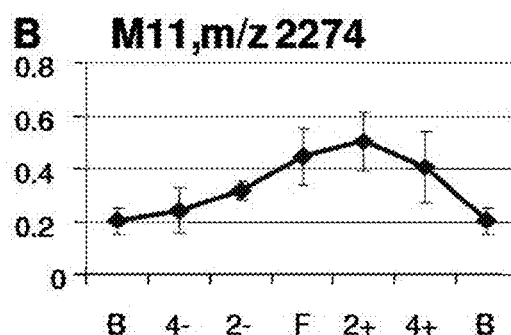
Figure 3C:
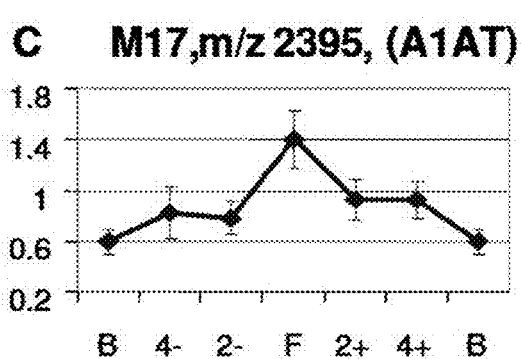
Figure 3D:
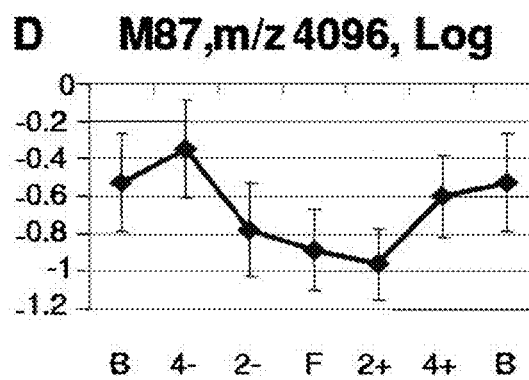

As illustrated, more protein ions progressively appear between 2000 and 4000 m/z as the flare develops, from an average of 18 peaks at baseline to 23 peaks at flare ($p<0.0001$). These proteins peaks disappear when the flare is effectively treated and renal SLE activity returns to baseline. Importantly, changes in the urine proteome can occur in either direction during the evolution of a flare, as shown by the decrease in some protein ions between pre-flare and flare (FIG. 2B).

Differentially Expressed Protein Ions

Twenty-seven protein ions showed significant differential expression between specific flare intervals, as shown in FIG. 8—Table 1.

To minimize false-positive results, candidate biomarkers were arbitrarily chosen from those protein ions that showed a change in expression of >1.5-fold. Of the 27 differentially-expressed protein ions, 25 met this criterion, were present in 32-92% of the flares, and were between 2000 and 10 000 m/z (FIG. 8—Table 1). Of the 27 protein ions in FIG. 8—Table 1, 16 fell between the baseline and pre-flare phases, 5 peaks between the pre-flare and flare phases, 7 peaks between the flare and post-flare phases, and 6 peaks were differentially-expressed over multiple intervals. Although no single peak appears in all of the SLE renal flares, several combinations of two peaks were observed in 100% of the flare cycles between remission and pre-flare, and between flare and post-flare (FIG. 9—Table 2).

The qualitative expression pattern of each candidate biomarker was examined throughout the flare cycle. Nineteen protein ions varied in parallel with the cycle, increasing or decreasing in intensity as flare approached, and then returning to baseline expression. Protein ions that fluctuated randomly over the flare cycle were not considered further as candidate biomarkers. The time-dependent expression of 4 representative candidate proteins is shown in FIG. 3.

Protein ions M1, M11 and M17 increased over the flare cycle while M87 decreased.

Effect of Immunosuppressive Medications

To determine if immunosuppressive medications affected urine SELDI-TOF-MS profiles, the correlations of prednisone, mycophenolate mofetil, and azathioprine dose to protein peak intensity 2 months pre-flare, at flare, and 2 months post-flare were calculated for 6 high frequency protein peaks (M8, M16, M17, M26, M28, M70).

Of the 54 possible linear regressions for this data set, 50 showed no significant correlation between medication dose and urine peptide level. Minor correlations between peak M16 at flare ($r^2=0.24$, $p=0.034$) and post-flare ($r^2=0.28$, $p=0.025$), and peak M70 post-flare ($r^2=0.24$, $p=0.022$) were observed with prednisone dose. Peak M26 displayed a strong positive correlation with prednisone dose at flare ($r^2=0.54$, $p=0.0004$), suggesting its urinary expression may have been enhanced by corticosteroids.

Peptide Identification

To demonstrate that candidate LMW urine biomarkers found by SELDI-TOF-MS screening can be positively identified, direct on-chip peptide sequencing was done for selected protein ions with a m/z less than 5000, that were expressed at high frequency, changed equal to or more than 1.5 fold between at least two phases of the flare cycle, and varied in parallel with the flare cycle. Using this technique, protein ions M8, M34, M17 and M26 were positively identified.

M8 and M34 correspond to the 20 and 25 amino acid (aa) isoforms of hepcidin (FIG. 4A). A 22 aa hepcidin isoform was also found in the urine of SLE patients (FIG. 4A), but was not differently expressed between any 2 phases of the flare cycle, and thus not considered a candidate biomarker. The time course of hepcidin expression is shown in FIG. 4B.

Hepcidin 20 (m/z 2198) increased 4 months pre-flare and then slowly returned to baseline by 4 months post-flare. Hepcidin 25 (m/z 2432) decreased at flare and returned to baseline by 4 months post-flare. There was no correlation between the 20 and 25 aa isoforms. There was no correlation between hepcidin 20 or 25 and eGFR ($r^2$=0.18, p=0.08; $r^2$=0.07, p=0.35, respectively).

Figure 4C:
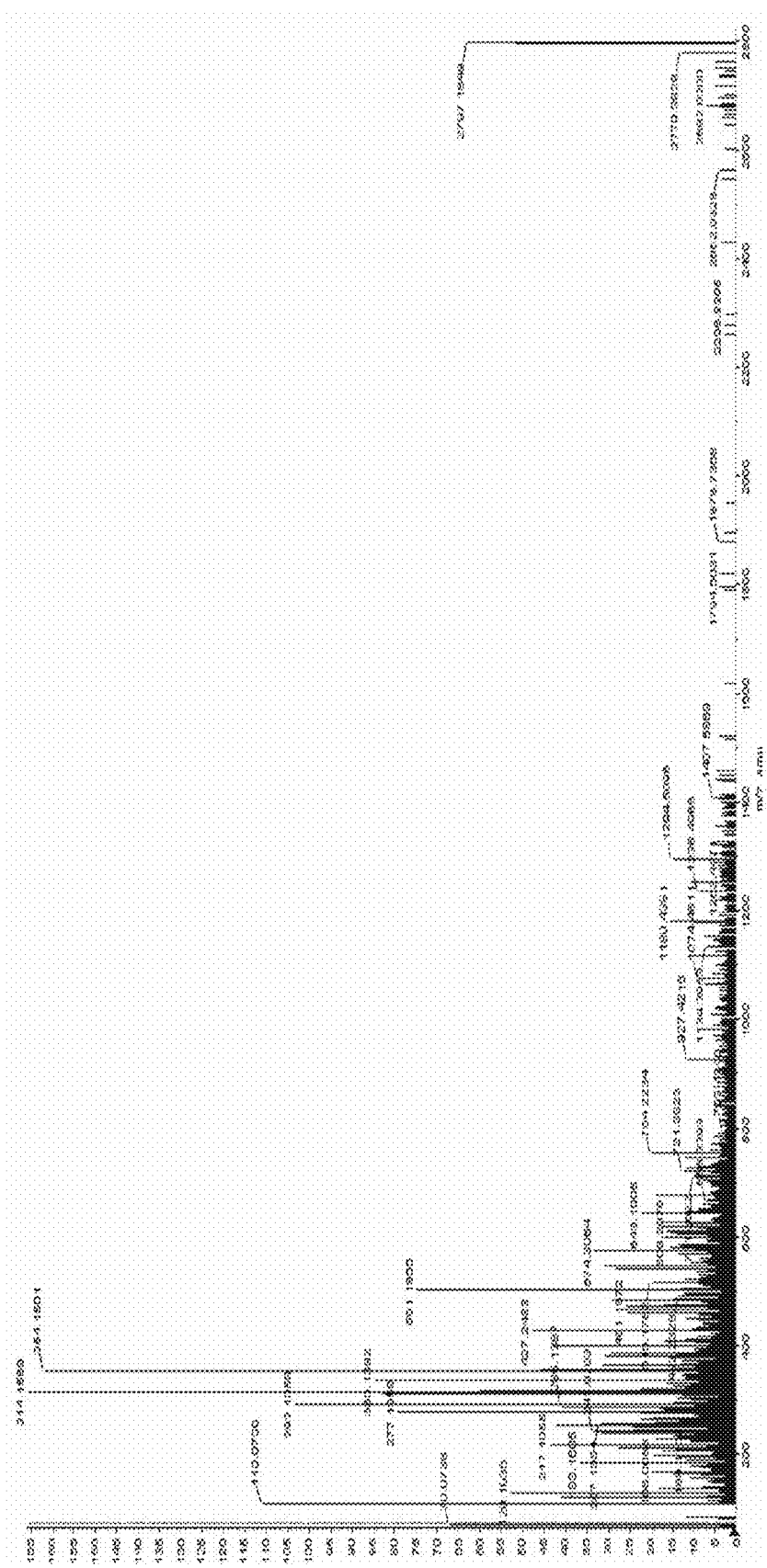
Figure 4D:
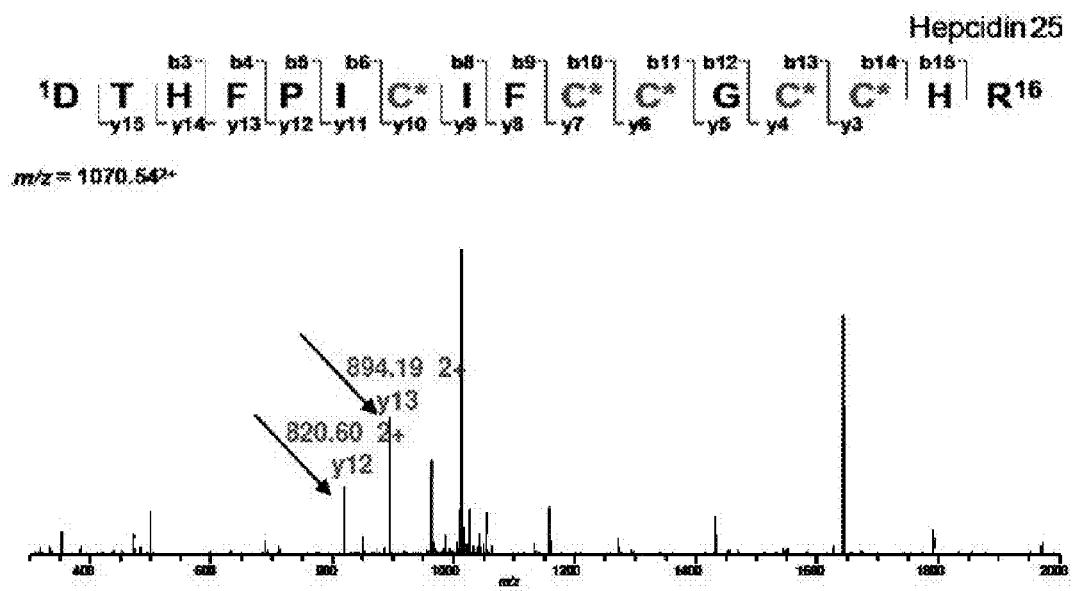
Figure 4E:
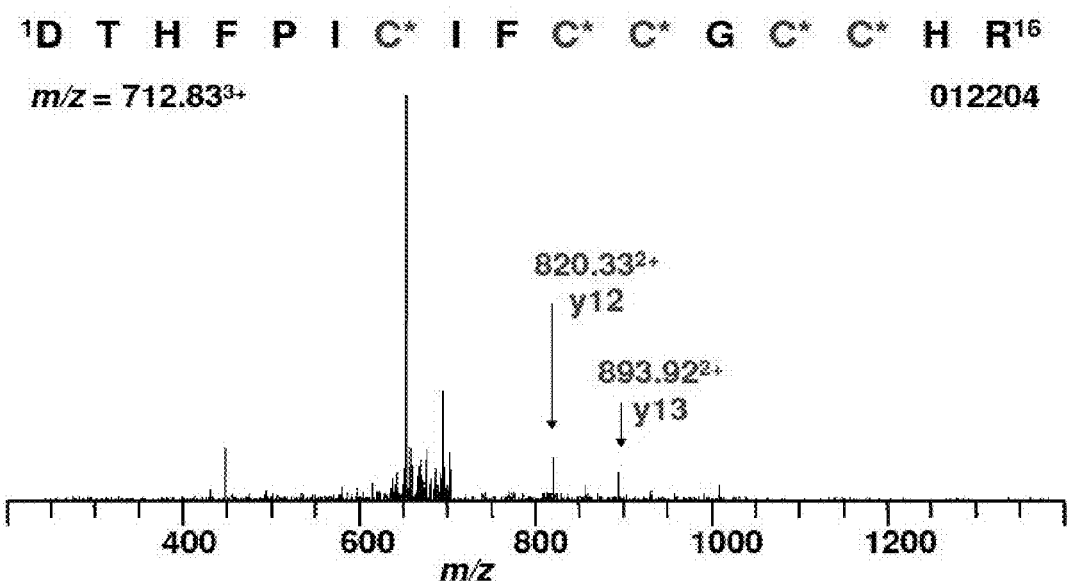

The presence of hepcidin in urine was further confirmed by LC/MS/MS from patients in whom hepcidin was identified by on-chip sequencing. FIG. 4C shows the on-chip CID fragmentation of urine hepcidin 25. FIG. 4D and FIG. 4E demonstrate LC/MS/MS detection of an internal peptide of hepcidin 25 (y-ions labeled) in the urine of an SLE patient.

Figure 5A:
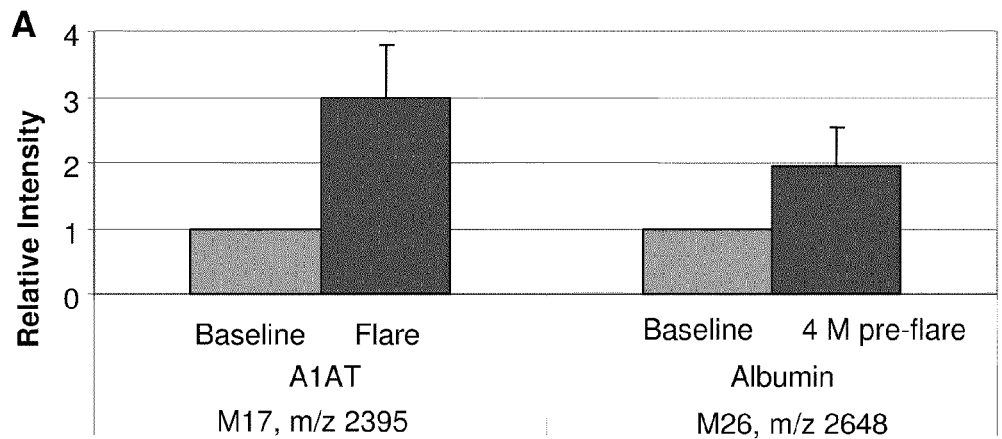
FIGS. 5A-5C depict urine expression of A1AT and an albumin fragment during SLE renal flare.
Figure 5B:
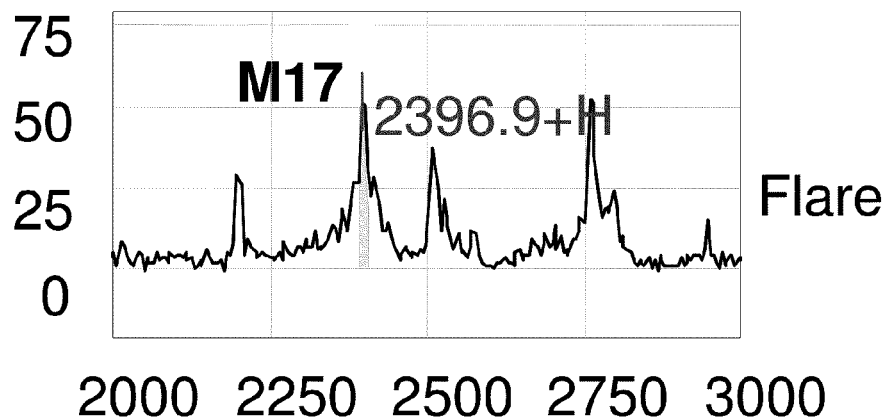
Figure 5C:
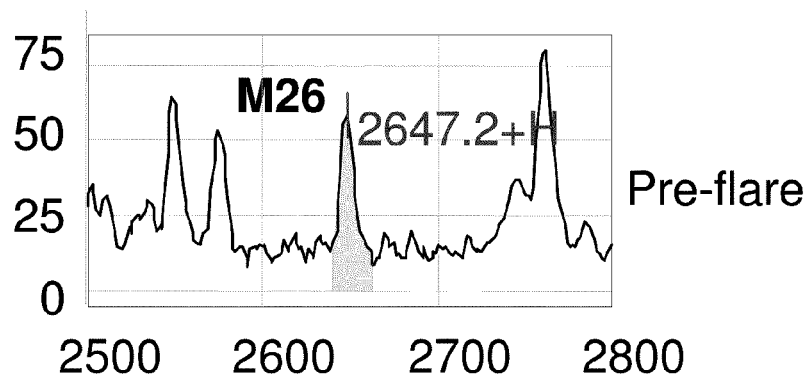

M17 (m/z 2395) and M26 (m/z 2648) correspond to a fragment of the 46 kDa precursor of a1-antitrypsin (A1AT), and a fragment of the N-terminal region of albumin, respectively. Both are abundant serum proteins. The A1AT fragment increased at flare, while the albumin fragment increased 4 month pre-flare compared to baseline (FIG. 5A). Corresponding SELDI spectra for A1AT and albumin are shown in FIG. 5B and FIG. 5C.

Renal Expression of Hepcidin

Biopsies from patients with SLE nephritis were stained for hepcidin, and infiltrating interstitial leukocytes were shown to express hepcidin (FIG. 6).

There was virtually no staining of renal parenchymal cells. Similarly, in a normal kidney the only cell stained was an interstitial cell, likely a resident macrophage. Hepcidin expression was minimal in the control kidney compared to SLE nephritis.

Discussion

This example demonstrates the usefulness of SELDI-TOF-MS as a screening technique to examine serial changes in the urine proteome of SLE patients during lupus nephritis flares. By understanding how specific urine proteins change as a renal flare develops, becomes clinically apparent, and is treated and resolves, it is believed by the inventors herein that clinically relevant biomarkers identified herein provide diagnostic, pathogenic, and therapeutic information on each phase of the flare cycle. Although SELDI-TOF-MS has been used to examine the urine proteome in a variety of conditions, including lupus nephritis, peptide expression patterns have mainly been described that differentiate between static disease states (23-25). Until now, few studies have used a longitudinal proteomic approach to identify specific proteins that can be verified and then validated in an independent sample set.

As described herein, the inventors examined the dynamic changes in the urine proteome over the SLE renal flare cycle and showed that hepcidin, A1AT, and an albumin fragment are differentially expressed during different phases of a nephritis flare. Interestingly, immunosuppressive medications had little effect on the expression of urine peptides detected by SELDI.

Hepcidin as Biomarker

Hepcidin is a low molecular weight (LMW) peptide hormone that has antimicrobial activity, regulates iron homeostasis, and has been implicated in the pathogenesis of the anemia of chronic inflammation, including that of chronic kidney disease (28-32). Hepcidin is mainly produced in the liver as pro-hepcidin, and undergoes N-terminal modification to yield the active C-terminal peptides of 20-25 aa, however other investigators have also found hepcidin in urine, and hepcidin 20 and 25 were dominant (28). Hepcidin may be made by renal tubular cells (33). Interestingly, the inventors herein did demonstrate intrarenal expression of hepcidin by infiltrating leukocytes in patients with SLE nephritis, raising the possibility that during renal flare hepcidin is produced within the kidney, rather than simply being filtered.

Urine hepcidin has been shown to increase during inflammation, and decline as inflammation resolved (34-36). Hepcidin expression is induced by interleukin-6 (IL-6) and is suppressed by TNF-a (31, 37), cytokines that are implicated in the pathogenesis of SLE (38-40). Therefore, the inventors herein determined that measurement of urine hepcidin isoforms during lupus flare may reflect the complex balance and changing expression of proinflammatory cytokines in lupus kidneys. Also, because expression of hepcidin 20 is altered pre-flare, is now believed by the inventors herein to be useful as a biomarker of impending renal flare.

In addition, the inventors herein now believe that that hepcidin 20 and 25 are regulated independently; that is, hepcidin 25 decreases at flare and increases during treatment. As such, the inventors herein now believe that hepcidin 25 is useful as a marker for following response to therapy. In this regard, urine hepcidin is now believed by the inventors herein to be useful as a lupus nephritis biomarker, and can be shown to be a better indicator of SLE activity than urine cytokines such as IL-6 or TNF-a (41, 42).

A1AT and albumin fragments were also found to be differentially expressed in the urine during SLE renal flare. Although the parent proteins are not from the LMW proteome, these findings still may be important in SLE nephritis. For example, A1AT is made in the kidney, and can be induced by cytokines such as IL-6 (43, 44). Thus, A 1 AT can serve as a marker of proinflammatory cytokine production. Furthermore, specific albumin and A1AT fragments have been found in the serum and urine of patients with glomerulonephritis (45). It is now believed that the fragmentation pattern of these proteins reflects pathogenic proteolytic activity during kidney disease, and the appearance of specific fragments in the urine can thus serve as a biomarker of this process. Conversely, charge variants of A1AT and albumin were found to be part of a group of urine proteins that could be used to distinguish between SLE and other proteinuric glomerular diseases (46). Characterization of the fragments of A1AT and albumin present throughout the SLE renal flare cycle can be performed to confirm whether fragments or charge variants of intact proteins, provide the most diagnostic information in SLE nephritis.

Despite the large number of protein peaks detected in raw urine, only 19 differentially expressed protein ions survived our moderately stringent criteria arbitrarily established for biomarker relevance to lupus nephritis. Furthermore, certain combinations of two candidate protein ions were found in all flare cycles, suggesting that validated biomarkers will be useful in most lupus patients, and that 2 or more biomarkers may be necessary to fully characterize phases of the flare cycle. These findings are consistent with other SELDI studies that showed only a few protein ions (3-13) were needed to separate disease from control groups, or predict kidney injury with high sensitivity and specificity (15, 16, 22, 23, 25). When SELDI-TOF-MS was used to distinguish between active and inactive SLE nephritis, it was reported that of 32 protein ions which varied significantly between active and quiescent SLE, a combination of two protein ions provided the most power for diagnosing active nephritis (24). Most of these studies used only one or two types of protein chips. While interrogating the entire proteome may require using a wide variety of protein chip binding surfaces, this technique is now believed to be capable of delivering a manageable number of candidate protein peaks. This can be if importance, considering the need to identify and validate each potential biomarker.

The examples herein show the usefulness of using SELDI-TOF-MS to screen for differential protein expression during the evolution of SLE renal flares. The method described herein yields a testable number of biomarker candidates that can then be specifically identified. The method described herein also eliminates the need for protein patterns as biomarkers, and allows validation and testing of candidate proteins in independent patient cohorts. Of three potential biomarkers identified herein, hepcidin is now believed to have a significant relationship to proinflammatory cytokines thought to mediate lupus nephritis.

Methods

Urine Samples

A total of 145 urine samples were obtained from the Ohio SLE Study (OSS) specimen bank. The OSS is a prospective, longitudinal study of patients with 4 or more American College of Rheumatology criteria for SLE, and has been described previously (47). The OSS was approved by the local IRB, and all patients gave informed consent to participate. Urine samples were from 19 patients with SLE nephritis who experienced 25 moderate to severe renal flares. The criteria used to adjudicate and classify the severity of renal flares in the OSS have been published (47). Urine was collected prospectively at 2 month intervals over several years from the OSS cohort. Fresh urine from each patient visit was centrifuged to remove cellular debris and rapidly frozen at −80° C. in small aliquots until use. Urine creatinine and protein concentrations were measured using the Roche Creatinine Reagent (Roche Diagnostic Corporation, Indianapolis, Ind.) and the Bio-Rad RC-DC Protein Assay (BioRad Laboratories, Hercules, Calif.), respectively.

Urine proteomes were examined from 4 phases of the SLE renal flare cycle: pre-flare, flare, treatment, and baseline. Pre-flare specimens were from 4 and 2 months before flare diagnosis, flare specimens were obtained at flare diagnosis, and treatment specimens were from 2 and 4 months after flare diagnosis. Baseline urines were chosen from specimens obtained more than 6 months away from any renal flare, and when patients had a stable serum creatinine and no proteinuria, or proteinuria values that had returned to pre-flare levels. Baseline samples could have preceded or followed the flare cycle under investigation, and in cases where both were available their data were combined to give a composite baseline.

To isolate the LMW urine proteome, urine protein size fractionation was done using VIVASPIN 500 spin columns (Vivascience, Carlsbad Calif.) having a molecular weight cut off of 30,000 Da to remove abundant, high-molecular weight proteins such as albumin. To avoid loss of LMW proteins bound to albumin, the urine was first denatured by adding 200 μl of urine to 300 μl of denaturing buffer (9M urea/2% CHAPS) for 30 min at 4° C. The denatured urine was then added to the spin columns and the flow-through was used for SELDI-TOF-MS analyses.

SELDI-TOF-MS Screening of the LMW Urine Proteome

Pilot experiments included protein chip selection and optimization of protein chip binding conditions. Among all the protein chips tested the best spectral data were obtained using a weak cation exchanger (CM10 chip, Ciphergen, Fremont, Calif.), which was subsequently used for this proof-of-concept study. All of the CM10 chips used in this example were from the same lot, samples were placed on the chips in random order, and as much as possible samples from the same patient were placed on a single chip. All data were acquired within 3 days, except for 2 chips that were read within 2 weeks. Fifty μl of urine sample mix (5 μl fractionated, denatured urine and 45 μl of 40 mM ammonium acetate pH 4.0, 0.1% Triton-X 100 buffer containing 10 fmol bovine insulin (Sigma, St. Louis, Mo.)) was added to each spot. The bovine insulin served as an internal standard for protein mass accuracy and was used to control for intra- and inter-chip variance of peak intensity. The linear binding range for insulin on CM10 ProteinChip is 1-50 fmol, and correlated to peak height with an $r^2$ of 0.99 at pH 4.0, a pH well below the insulin pI of 5.65 (data not shown). Using endogenous urine protein ions normalized to bovine insulin, the intra-chip coefficient of variation (CV) for peak height was 11% and inter-chip CV was 19.7%, values compatible to or better than those previously reported (18, 24). After binding, chips were washed, dried and 1.0 μl of an energy absorbing molecule (30% CHCA in 50% Acetonitrile (ACN) and 0.5% Trifluoroacetic Acid (TFA)), was added.

Urine protein spectra were acquired with a Protein Chip PBS II Reader (Ciphergen) set to an optimum mass range of 500-20 000 Da, a laser intensity of 195 with 2 warming shots (not collected), a sensitivity of 9, and collection of 50 transient shots across the spot surface. To minimize the protein chip spot variance, each urine sample was done on duplicate spots. External calibration of the Protein Chip Reader was performed using the Ciphergen Biosystem All-in-1 peptide standard C100-0005, and the calibration equation was applied to each spectrum before analysis to ensure the peak accuracy.

Data Analysis

Figure 1:
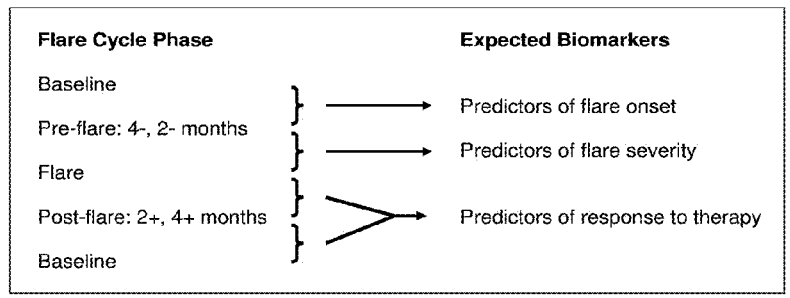
FIG. 1 depicts an analysis scheme for urine protein phenotyping of SLE nephritis flare cycle.

Protein peaks were detected by second-pass peak selection and restricted to a signal-to-noise ratio of >2, minimum valley depth of 2 and sensitivity of 100%. The mass range from 2000-20 000 Da was selected for analysis since this range contained the majority of the resolved. protein/peptides. The detected peaks from different patients were aligned manually according to the peak accuracy variance, which was less than 0.5% for the internal insulin calibration standard (data not shown). Only peaks present in more than 30% of the flares were analyzed further, in an effort to screen for biomarkers of general applicability to SLE nephritis. The spectra were normalized to the total ion current within duplicates to minimize the protein chip spot variance. The intensity of each peak in the spectra was then further normalized to the internal insulin control, and urine creatinine concentration to account for urine dilution. Protein peaks were compared stepwise between 2 phases of the renal flare cycle, as illustrated in FIG. 1.

Data were analyzed by the paired t-test or the Wilcoxon matched pairs test, based on whether they were or were not normally distributed. These statistical tests rather than repeated measures ANOVA were used because the standard deviation of the data was not stable over time. A two-tailed alpha level of <0.05 was considered significant.

Peptide Identification

For direct on-chip peptide sequencing and identification (48) the CM10 chip was reduced by with DTT and selected, differentially-expressed peptide ions less than 5000 Da were sequenced. Sequence data were obtained using a Protein Chip Tandem MS Interface with a front-end SELDI ion source for the Applied Biosystem/MDS Sciex QStar Hybrid LC/MS/MS System (Ciphergen, Fremont, Calif.). The protein chip interface used a 337 nm nitrogen laser with a lensed fiber optic, delivering 150 mJ of energy per pulse at 30 pulses/second. Peptides underwent collision-induced dissociation (CID) by applied collision energy of 50 eV/kDa. Sample spot scanning was controlled via Protein Chip Interface Control Software (Bio-Rad Laboratories), while data analysis and acquisition were carried out using the QStar System's Analyst software (Applied Biosystems, Inc. Foster City, Calif.). This system is capable of high amole-low fmole MS and MS/MS sensitivity. The sequences resulting from spectral data were submitted to the database mining tool Mascot (49) for identification.

Results of on-chip identification were further confirmed using Nano-LC/MS/MS at the Ohio State Mass Spectrometry and Proteomics Facility. Briefly, urine samples and human hepcidin 20 and 25 peptide standards (Alpha Diagnostics International Inc, San Antonio, Tex.) were digested in trypsin and Nano-LC/MS/MS was performed on a Thermo Finnigan LTQ mass spectrometer (Waltham, Mass.) equipped with a nanospray source operated in positive ion mode. The LC system was an UltiMate™ Plus system from LC-Packings A Dionex Co (Sunnyvale, Calif.) with a Famos autosampler and Switchos column switcher. The scan sequence of the mass spectrometer was based on the TopTen™ method. Analysis was programmed for a full scan recorded between 350-2000 Da, and a MS/MS scan to generate product ion spectra to determine amino acid sequence in consecutive instrument scans of the ten most abundant peaks in the spectrum. Sequence information from the MS/MS data was converted to a merged file and then was searched using Mascot Daemon version 2.2.1 by Matrix Science (Boston, Mass.) and the database searched against the full SwissProt database version 54.1 (283454 sequences; 104030551 residues). Protein identifications were checked manually and proteins with a Mascot score of 50 or higher with a minimum of two unique peptides from one protein having a −b or −y ion sequence tag of five residues or better were accepted.

Immunohistochemistry

Renal biopsy material from 3 cases of class IV lupus nephritis, and one normal transplant donor kidney were stained with a rabbit anti-hepcidin polyclonal antibody (AB-CAM), and visualized with DAB. Paraffin embedded tissue was used, endogenous peroxidase was quenched with hydrogen peroxide, and antigen retrieval was done with citric acid (pH 6.1) for 25 minutes at 94° C. before incubation with the primary antibody (1:500) overnight at 4° C. No staining was observed with a non-immune control antibody.

Peripheral Blood Mononuclear Cell (PBMC)

FIG. 7A demonstrates in two different human Peripheral Blood Mononuclear Cell (PBMC) samples that interferon-alpha increase hepcidin mRNA expression in a dose-dependent fashion. This is important because interferon-alpha is believed to be a key cytokine whose activation is relevant to human SLE nephritis.

FIG. 7B demonstrates in two different human PBMC samples the effects of a variety of other cytokines on hepcidin mRNA expression. As can be seen, MCP-1 a monocyte chemokine induces expression of hepcidin, and TNF-alpha suppresses expression. This is important because MCP-1 is a biomarker of active SLE nephritis and is greatly increased in the kidney and urine during SLE kidney flare. Also, TNF-alpha has been postulated to have a role in SLE as well.

Longitudinal profiling of the hepcidin isoforms revealed that hepcidin-20 increases as early as four (4) months before a flare episode and hepcidin-25 decreases as early as two (2) months before the flare episode.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

The citation of any reference herein is not an admission that such reference is available as prior art to the instant invention. Any publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

1. Brown F G, Nikolic-Paterson D J, Hill P A, et al. Urine macrophage migration inhibitory factor reflects the severity of renal injury in human glomerulonephritis. J Am Soc Nephrol. 2002; 13:S7-S13.
2. Fiehn C, Hajjar Y, Mueller K, et al. Improved clinical outcome of lupus nephritis during the past decade: importance of early diagnosis and treatment. Ann Rheum Dis. 2003; 62:435-9.
3. Houssiau F A, Vasconcelos C, D'Cruz D, et al. Early response to immunosuppressive therapy predicts good renal outcome in lupus nephritis. Arthritis Rheum. 2004; 50:3934-40.
4. Illei G G, Tackey E, Lapteva L, Lipsky P E. Biomarkers in systemic lupus erythematosus: General overview of biomarkers and their applicability. Arthritis Rheum. 2004; 50:1709-20.
5. Illei G G, Tackey E, Lapteva L, Lipsky P E. Biomarkers in systemic lupus erythematosus: Markers of disease activity. Arthritis Rheum. 2004; 50:2048-65.
6. Schiffenbauer J, Hahn B, Weisman M H, Simon L S. Biomarkers, surrogate markers, and design of clinical trials of new therapies for systemic lupus erythematosus. Arthritis Rheum. 2004; 50:2415-22.
7. Harry J L, Wilikins M R, Herbert B R, et al. Proteomics: Capacity versus utility. Electrophoresis. 2000; 21:1071-81.
8. James P. Protein identification in the post-genome era: the rapid rise of proteomics. Q Rev Biophys. 1997; 30(4):279-331.
9. Piubelli C, Galvani M, Hamdan M, et al. Proteome analysis of rat polymorphonuclear leukocytes: A two-dimensional electrophoresis/mass spectrometry approach. Electrophoresis. 2002; 23:298-310.
10. Rai A J, Zhang Z, Rosenzweig J, et al. Proteomic approaches to tumor marker discovery: Identification of biomarkers for ovarian cancer. Arch Pathol Lab Med. 2002; 126:1518-26.

11. Knepper M A. Proteomics and the kidney. J Am Soc Nephrol. 2002; 13:1398-408.
12. Oates J C, Varghese S, Bland A M, et al. Prediction of urinary protein markers in lupus nephritis. Kidney Int. 2005; 68:2588-92.
13. Reddy G, Dalmasso EA. SELDI ProteinChip array technology: Protein-based predictive medicine and drug discovery applications. J Biomed Biotech. 2003; 4:237-41.
14. Stone J H, Rajapakse V N, Hoffman G S, et al. A serum proteomic approach to gauging the state of remission in Wegener's granulomatosis. Arthritis Rheum. 2005; 52:902-10.
15. Voshol H, Brendlen N, Muller D, et al. Evaluation of biomarker discovery approaches to detect protein biomarkers of acute renal allograft rejection. J Prot Res. 2005; 4:1192-9.
16. Hampel D J, Sansome C, Sha M, et al. Toward proteomics in uroscopy: Urinary protein profiles after radiocontrast medium administration. J Am Soc Nephrol. 2001; 12:1026-35.
17. Schaub S, Wilkins J, Weiler T, et al. Urine protein profiling with surface-enhanced laser-desorption/ionization time-of-flight mass spectrometry. Kidney Int. 2004; 65:323-32.
18. Ranganathan S, Williams E, Ganchev P, et al. Proteomic profiling of cerebrospinal fluid identifies biomarkers for amyotrophic lateral sclerosis. J Neurochem. 2005; 95:1461-71.
19. Soltys S G, Le Q-T, Shi G, Tibshirani R, et al. The use of plasma surface-enhanced laser desorption/ionization time-of-flight mass spectrometry proteomic patterns for detection of head and neck squamous cell cancers. Clin Can Res. 2004; 10:4806-12.
20. Vlahou A, Schellhammer P, Mendrinos S, et al. Development of a novel proteomic approach for the detection of transitional cell carcinoma of the bladder in urine. Am J Pathol. 2001; 158:1491-502.
21. Rogers M A, Clarke P, Noble J, et al. Proteomic profiling of urinary proteins in renal cancer by surface enhanced laser desorption ionization and neural-network analysis: identification of key issues affecting potential clinical utility. Can Res. 2003; 63:6971-83.
22. Clark W, Silverman B C, Zhang Z, et al. Characterization of renal allograft rejection by urinary proteomic analysis. Ann Surg. 2003; 237:660-4.
23. Schaub S, Rush D, Wilkins J, et al. Proteomic-based detection of urine proteins associated with renal allograft rejection. J Am Soc Nephrol. 2004; 15:219-27.
24. Mosley K, Tam F W K, Edwards R J, Crozier J, et al. Urinary proteomic profiles distinguish between active and inactive SLE nephritis. Rheumatol. 2006; in press.
25. O'Riordan E, Orlova T N, Mei J, et al. Bioinformatic analysis of the urine proteome of acute allograft rejection. J Am Soc Nephrol. 2004; 15:3240-8.
26. Schaub S, Wilkins J A, Antonovici M, et al. Proteomic-based identification of cleaved urinary beta-microglobulin as a potential marker for acute tubular injury in renal allografts. Am J Transplant. 2005; 5:729-238.
27. Suzuki M, Ross G F, Wiers K, et al. Identification of a urinary proteomic signature for lupus nephritis in children. Pediatr Nephrol. 2007; 22:2047-57.
28. Yang C W, Ahn H J, Han H J, et al. Pharmacological preconditioning with low-dose cyclosporine or FK506 reduces subsequent ischemia/reperfusion injury in rat kidney. Transplantation. 2001; 72:1753-9.
29. Malyszko J, Malyszko J S, Brzosko S, et al. Adiponectin is related to CD146, a novel marker of endothelial cell activation/injury in chronic renal failure and peritoneally dialyzed patients. J Clin Endo Metab. 2004; 89:4620-7.
30. Deicher R, Horl W H. Hepcidin: a molecular link between inflammation and anaemia. Nephrol Dial Transplant. 2004; 19:521-4.
31. Nemeth E, Rivera S, Gabayan V, et al. IL-6 mediates hypoferremia of inflammation by inducing the synthesis of the iron regulatory hormone hepcidin. J Clin Invest. 2004; 113:1271-6.
32. Andrews N C. Anemia of inflammation: the cytokine-hepcidin link. J Clin Invest. 2004; 113:1251-3.
33. Kulaksiz H, Theilig F, Bachmann S, et al. The iron-regulatory peptide hormone hepcidin: expression and cellular localization in the mammalian kidney. J Endo. 2005; 184:361-70.
34. Kemna E H J M, Pickkers P, Nemeth E, et al. Time-course analysis of hepcidin, serum iron, and plasma cytokine levels in humans injected with LPS. Blood. 2005; 106:1864-6.
35. Kemna E H J M, Tjalsma H, Laarakkers C, et al. Novel urine hepcidin assay by mass spectrometry. Blood. 2005; 106:3268-70.
36. Nemeth E, Valore E V, Territo M, et al. Hepcidin, a putative mediator of anemia of inflammation, is a type II acute-phase protein. Blood. 2003; 101:2461-3.
37. Lee P, Peng H, Gelbart T, et al. Regulation of hepcidin transcription by interleukin-1 and interleuking-6. Proc Natl Acad Sci USA. 2005; 102:1906-10.
38. Tackey E, Lipsky P E, Illei G G. Rationale for interleukin-6 blockade in systemic lupus erythematosus. Lupus. 2004; 13:339-43.
39. Mongan A E, Ramdahin S, Warrington R J. Interleukin-10 response abnormalities in systemic lupus erythematosus. Scand J Immunol. 1997; 46(4):406-12.
40. Aringer M, Smolen J S. Cytokine expression in lupus kidneys. Lupus. 2005; 14:13-8.
41. Li Y, Tucci M, Narain S, et al. Urinary biomarkers in lupus nephritis. Autoimmunity Rev. 2006; 5:383-8.
42. Tesar V, Masek Z, Rychlik I, et al. Cytokines and adhesion molecules in renal vasculitits and lupus nephritis. Nephrol Dial Transplant. 1998; 13:1662-7.
43. Drew P D, Franzoso G, Carlson L M, et al. Interferon regulatory factor-2 physically interacts with NF-kappaB in vitro and inhibits NF-kappaB induction of major histocompatibility class I and beta-2-microglobulin gene expression in transfected human neuroblastoma cells. J Neuroimmunol. 1995; 63:157-62.
44. Perlmutter D H, May L T, Sehgal P B. Interferon beta 2/interleukin 6 modulates synthesis of alpha 1 antitrypsin in human mononuclear phagocytes and in human hepatoma cells. J Clin Invest. 1989; 84:138-44.
45. Candiano G, Musante L, Bruschi M, et al. Repetitive fragmentation products of albumin and alpha1-antitrypsin in glomerular diseases associated with nephrotic syndrome. J Am Soc Nephrol. 2006; 17:3139-48.
46. Varghese S A, Powell T B, Budisavljevic M N, et al. Urine biomarkers predict the cause of glomerular disease. J Am Soc Nephrol. 2007; 18:913-22.
47. Rovin B H, Song H, Birmingham D J, et al. Urine chemokines as biomarkers of human systemic lupus erythematosus activity. J Am Soc Nephrol. 2005; 16:467-73.
48. Caputo E, Moharram R, Martin B M. Methods for on-chip protein analysis. Anal Biochem. 2003; 321:116-24.-n
49. Kemna E H J M, Tjalsma H, Podust V N, Swinkels D W. Mass spectrometry-based hepcidin measurements in serum and urine: Analytical aspects and clinical implications. Clin Chem. 2007; 53:620-8.

What is claimed is:

1. A method of analyzing a subject sample to identify at least a beginning of a kidney flare episode in a subject suffering from systemic lupus erythematosus (SLE), comprising:
   i) assaying at least one urine sample from the subject for the amounts of hepcidin-20 and hepcidin-25, and
   ii) characterizing the subject's risk of having a kidney flare episode within about four months based upon the amounts of hepcidin-20 and hepcidin-25 measured in the at least one urine sample,
   wherein the subject is characterized as being at risk of having a kidney flare episode within about four months when there is an increase in hepcidin-20 and a decrease in hepcidin-25 in the at least one urine sample, as compared to predetermined threshold levels.

2. The method of claim 1, wherein the predetermined threshold levels comprise levels of hepcidin-20 and hepcidin-25 measured in at least one additional urine sample taken from the subject at a point in time prior to the assaying step i).

3. The method of claim 1, wherein the method further includes assaying at least one additional urine sample taken from the subject taken at a point in time prior to the assaying of the at least one urine sample in step i).

4. The method of claim 1, wherein the method further includes assaying at least one additional urine sample taken from the subject taken at a point in time after the assaying of the at least one urine sample in step i).

5. A diagnostic method, comprising:
   determining the concentrations of hepcidin-20 and hepcidin-25 in a urine sample from a subject suffering from systemic lupus erythematosus,
   and diagnosing the subject as being likely to suffer a kidney flare episode within about four months when the hepcidin-20 concentration in the urine sample is increased relative to a threshold hepcidin-20 concentration and the hepcidin-25 concentration in the urine sample is decreased relative to a threshold hepcidin-25 concentration;
   wherein a lack of an increase in hepcidin-20 in the sample relative to the threshold hepcidin-20 concentration and a lack of a decrease in hepcidin-25 concentration relative to the threshold hepcidin-25 concentration indicates that a kidney flare episode is not likely to occur in the subject within about four months.

6. The method of claim 5, wherein the increase in hepcidin-20 is present at about four months prior to presentation of symptoms of the kidney flare episode.

7. The method of claim 5, wherein the decrease in hepcidin-25 is present at about two months prior to presentation of symptoms of the kidney flare episode.

* * * * *

SEQUENCE LISTING

<160> NUMBER OF SEQ ID NOS: 3

<210> SEQ ID NO 1
<211> LENGTH: 25
<212> TYPE: PRT
<213> ORGANISM: Homo sapiens

<400> SEQUENCE: 1

Asp Thr His Phe Pro Ile Cys Ile Phe Cys Cys Gly Cys Cys His Arg
 1               5                  10                  15

Ser Lys Cys Gly Met Cys Cys Lys Thr
            20                  25

<210> SEQ ID NO 2
<211> LENGTH: 20
<212> TYPE: PRT
<213> ORGANISM: Homo sapiens

<400> SEQUENCE: 2

Ile Cys Ile Phe Cys Cys Gly Cys Cys His Arg Ser Lys Cys Gly Met
 1               5                  10                  15

Cys Cys Lys Thr
            20

<210> SEQ ID NO 3
<211> LENGTH: 16
<212> TYPE: PRT
<213> ORGANISM: Homo sapiens

<400> SEQUENCE: 3

Asp Thr His Phe Pro Ile Cys Ile Phe Cys Cys Gly Cys Cys His Arg
 1               5                  10                  15